(12) United States Patent
Connors et al.

(10) Patent No.: US 7,465,307 B2
(45) Date of Patent: *Dec. 16, 2008

(54) TISSUE TREATMENT SYSTEM

(75) Inventors: Kevin P. Connors, San Francisco, CA (US); David A. Gollnick, Foster City, CA (US); Michael W. Sasnett, Los Altos, CA (US); Dean A. MacFarland, Magnolia, MA (US)

(73) Assignee: Cutera, Inc., Brisbane, CA (US)

( * ) Notice: Subject to any disclaimer, the term of this patent is extended or adjusted under 35 U.S.C. 154(b) by 178 days.

This patent is subject to a terminal disclaimer.

(21) Appl. No.: 11/265,716

(22) Filed: Nov. 2, 2005

(65) Prior Publication Data

US 2006/0122585 A1 Jun. 8, 2006

Related U.S. Application Data

(60) Continuation of application No. 10/687,040, filed on Oct. 16, 2003, now Pat. No. 7,041,094, which is a continuation of application No. 09/998,821, filed on Nov. 15, 2001, now Pat. No. 6,666,856, which is a division of application No. 09/270,118, filed on Mar. 15, 1999, now Pat. No. 6,383,176.

(60) Provisional application No. 60/124,450, filed on Mar. 15, 1999, provisional application No. 60/124,709, filed on Mar. 15, 1999.

(51) Int. Cl.
*A61N 5/06* (2006.01)

(52) U.S. Cl. .............................. 606/88; 607/89; 606/9; 606/10; 606/23

(58) Field of Classification Search ............ 607/88–91; 606/3, 9–12, 20, 22, 23; 128/898
See application file for complete search history.

(56) References Cited

U.S. PATENT DOCUMENTS

| 2,699,771 A | 1/1955 | Rüttger-Pelli | 128/24.1 |
| 3,327,712 A | 6/1967 | Kaufman et al. | 128/398 |
| 3,538,919 A | 11/1970 | Meyer | 606/36 |

(Continued)

FOREIGN PATENT DOCUMENTS

| CA | 968854 | 6/1975 | 326/4 |

(Continued)

OTHER PUBLICATIONS

Anderson, "Clinical Use of the LightSheer Diode Laser System," *Harvard Medical School*, Reprint, Mar. 1998.

(Continued)

*Primary Examiner*—Ahmed M Farah
(74) *Attorney, Agent, or Firm*—Stallman & Pollock LLP

(57) ABSTRACT

A hair removal device (22) includes a cooling surface (34) which is used to contact the skin (6) prior to exposure to hair tissue-damaging laser light (74) passing from a radiation source (36) through a recessed window (46). The window is laterally offset from the cooling surface and is spaced apart from the cooling surface in a direction away from the patient's skin to create a gap between the window and the skin. The window preferably includes both an inner window (46) and an outer, user-replaceable window (48). The laser-pulse duration is preferably selected according to the general diameter of the hair.

10 Claims, 20 Drawing Sheets

U.S. PATENT DOCUMENTS

| | | | |
|---|---|---|---|
| 3,648,706 A | 3/1972 | Holzer | 128/395 |
| 3,693,623 A | 9/1972 | Harte et al. | 606/9 |
| 3,834,391 A | 9/1974 | Block | 606/9 |
| 3,867,948 A | 2/1975 | Kallenborn | 128/395 |
| 3,900,034 A | 8/1975 | Katz et al. | 607/89 |
| 4,020,383 A | 4/1977 | Labadini et al. | 313/344 |
| 4,022,534 A | 5/1977 | Kishner | 356/210 |
| 4,122,853 A | 10/1978 | Smith | 606/4 |
| 4,233,493 A | 11/1980 | Nath | 219/354 |
| 4,298,005 A | 11/1981 | Mutzhas | 128/396 |
| 4,388,924 A | 6/1983 | Weissman et al. | 606/9 |
| 4,461,294 A | 7/1984 | Baron | 606/5 |
| 4,505,545 A | 3/1985 | Salia-Munoz | 350/321 |
| 4,539,987 A | 9/1985 | Nath et al. | 128/303.1 |
| 4,608,978 A | 9/1986 | Rohr | 606/9 |
| 4,608,990 A | 9/1986 | Elings | 128/633 |
| 4,617,926 A | 10/1986 | Sutton | 606/9 |
| 4,658,823 A | 4/1987 | Beddoe et al. | 128/396 |
| 4,667,658 A | 5/1987 | Guibert | 128/24.1 |
| 4,686,986 A | 8/1987 | Fenyö et al. | 128/396 |
| 4,733,660 A | 3/1988 | Itzkan | 606/9 |
| 4,747,660 A | 5/1988 | Nishioka et al. | 350/96.25 |
| 4,757,431 A | 7/1988 | Cross et al. | 362/261 |
| 4,784,135 A | 11/1988 | Blum et al. | 128/303.1 |
| 4,813,412 A | 3/1989 | Yamazaki et al. | 128/303.13 |
| 4,819,669 A | 4/1989 | Politzer | 132/200 |
| 4,829,262 A | 5/1989 | Furumoto | 359/346 |
| 4,860,172 A | 8/1989 | Schlager et al. | 362/32 |
| 4,884,568 A | 12/1989 | Hahn | 128/303.1 |
| 4,917,084 A | 4/1990 | Sinofsky | 606/7 |
| 4,930,504 A | 6/1990 | Diamantopoulos et al. | 128/395 |
| 4,950,880 A | 8/1990 | Hayner | 250/201.9 |
| 4,976,709 A | 12/1990 | Sand | 606/5 |
| 5,000,752 A | 3/1991 | Hoskin et al. | 606/9 |
| 5,057,104 A | 10/1991 | Chess | 606/9 |
| 5,059,192 A | 10/1991 | Zaias | 606/9 |
| 5,139,494 A | 8/1992 | Freiberg | 606/3 |
| 5,161,526 A | 11/1992 | Hellwing et al. | 128/395 |
| 5,182,857 A | 2/1993 | Simon | 30/34.05 |
| 5,207,671 A | 5/1993 | Franken et al. | 606/9 |
| 5,217,455 A | 6/1993 | Tan | 606/9 |
| 5,226,907 A | 7/1993 | Tankovich | 606/133 |
| 5,258,989 A | 11/1993 | Raven | 372/6 |
| 5,259,380 A | 11/1993 | Mendes et al. | 607/115 |
| 5,282,797 A | 2/1994 | Chess | 606/9 |
| 5,290,273 A | 3/1994 | Tan | 606/9 |
| 5,304,169 A | 4/1994 | Sand | 606/5 |
| 5,304,170 A | 4/1994 | Green | 606/9 |
| 5,312,395 A | 5/1994 | Tan et al. | 606/9 |
| 5,320,618 A | 6/1994 | Gustafsson | 606/9 |
| 5,336,217 A | 8/1994 | Buys et al. | 606/9 |
| 5,337,741 A | 8/1994 | Diamond | 600/8 |
| 5,344,418 A | 9/1994 | Ghaffari | 606/9 |
| 5,344,434 A | 9/1994 | Talmore | 607/88 |
| 5,374,265 A | 12/1994 | Sand | 606/5 |
| 5,397,327 A | 3/1995 | Koop et al. | 606/17 |
| 5,405,368 A | 4/1995 | Eckhouse | 607/88 |
| 5,409,479 A | 4/1995 | Dew et al. | 606/9 |
| 5,425,728 A | 6/1995 | Tankovich | 606/9 |
| 5,441,531 A | 8/1995 | Zarate et al. | 607/90 |
| 5,458,596 A | 10/1995 | Lax et al. | 606/31 |
| 5,474,549 A | 12/1995 | Ortiz et al. | 606/9 |
| 5,486,172 A | 1/1996 | Chess | 606/20 |
| 5,511,563 A | 4/1996 | Diamond | 128/848 |
| 5,522,813 A | 6/1996 | Trelles | 606/2 |
| 5,527,350 A | 6/1996 | Grove et al. | 607/89 |
| 5,569,979 A | 10/1996 | Scott et al. | 313/636 |
| 5,572,091 A | 11/1996 | Langer et al. | 313/636 |
| 5,591,157 A | 1/1997 | Hennings et al. | 606/3 |
| 5,595,568 A | 1/1997 | Anderson et al. | 606/9 |
| 5,611,795 A | 3/1997 | Slatkine et al. | 606/9 |
| 5,620,478 A | 4/1997 | Eckhouse | 607/88 |
| 5,660,836 A | 8/1997 | Knowlton | 424/400 |
| 5,683,380 A | 11/1997 | Eckhouse et al. | 606/9 |
| 5,735,844 A * | 4/1998 | Anderson et al. | 606/9 |
| 5,755,753 A | 5/1998 | Knowlton | 607/98 |
| 5,769,844 A | 6/1998 | Ghaffari | 606/16 |
| 5,769,878 A | 6/1998 | Kamei | 607/88 |
| 5,782,895 A | 7/1998 | Zarate et al. | 607/88 |
| 5,807,261 A | 9/1998 | Benaron et al. | 600/473 |
| 5,810,801 A | 9/1998 | Anderson et al. | 606/9 |
| 5,814,040 A | 9/1998 | Nelson et al. | 606/9 |
| 5,820,625 A | 10/1998 | Izawa et al. | 606/9 |
| 5,830,208 A * | 11/1998 | Muller | 606/9 |
| 5,843,074 A | 12/1998 | Cocilovo | 606/10 |
| 5,843,143 A | 12/1998 | Whitehurst | 607/88 |
| 5,885,274 A | 3/1999 | Fullmer et al. | 606/9 |
| 5,919,219 A | 7/1999 | Knowlton | 607/102 |
| 5,964,749 A | 10/1999 | Eckhouse et al. | 606/9 |
| 5,989,283 A | 11/1999 | Wilkens | 607/88 |
| 6,015,404 A | 1/2000 | Altshuler et al. | 606/9 |
| 6,050,990 A | 4/2000 | Tankovich et al. | 606/9 |
| 6,067,241 A * | 5/2000 | Lu | 363/65 |
| 6,080,146 A | 6/2000 | Altshuler et al. | 606/9 |
| 6,080,147 A | 6/2000 | Tobinick | 606/9 |
| 6,096,066 A | 8/2000 | Chen et al. | 607/88 |
| 6,120,497 A | 9/2000 | Anderson et al. | 606/9 |
| 6,168,590 B1 | 1/2001 | Neev | 606/9 |
| 6,171,332 B1 | 1/2001 | Whitehurst | 607/89 |
| 6,228,074 B1 | 5/2001 | Almeida | 606/9 |
| 6,235,015 B1 | 5/2001 | Mead, III et al. | 606/9 |
| 6,241,753 B1 | 6/2001 | Knowlton | 607/99 |
| 6,264,649 B1 * | 7/2001 | Whitcroft et al. | 606/22 |
| 6,273,884 B1 | 8/2001 | Altshuler et al. | 606/9 |
| 6,280,438 B1 | 8/2001 | Eckhouse et al. | 606/9 |
| 6,319,273 B1 | 11/2001 | Chen et al. | 607/88 |
| 6,377,855 B1 | 4/2002 | Knowlton | 607/101 |
| 6,381,498 B1 | 4/2002 | Knowlton | 607/101 |
| 6,383,176 B1 * | 5/2002 | Connors et al. | 606/9 |
| 6,387,089 B1 | 5/2002 | Kreindel et al. | 606/9 |
| 6,405,090 B1 | 6/2002 | Knowlton | 607/102 |
| 6,413,253 B1 | 7/2002 | Koop et al. | 606/27 |
| 6,443,978 B1 | 9/2002 | Zharov | 607/91 |
| 6,453,202 B1 | 9/2002 | Knowlton | 607/102 |
| 6,461,866 B1 | 10/2002 | Whitehurst | 435/325 |
| 6,482,199 B1 | 11/2002 | Neev | 606/10 |
| 6,485,484 B1 * | 11/2002 | Connors et al. | 606/9 |
| 6,508,813 B1 | 1/2003 | Altshuler | 606/9 |
| 6,517,532 B1 | 2/2003 | Altshuler et al. | 606/9 |
| 6,558,372 B1 | 5/2003 | Altshuler | 606/2 |
| 6,569,155 B1 | 5/2003 | Connors et al. | 606/9 |
| 6,573,063 B2 | 6/2003 | Hochman | 435/29 |
| 6,602,275 B1 | 8/2003 | Sullivan | 607/88 |
| 6,605,080 B1 | 8/2003 | Altshuler et al. | 606/3 |
| 6,638,272 B2 * | 10/2003 | Cho et al. | 606/13 |
| 6,663,620 B2 | 12/2003 | Altshuler et al. | 606/9 |
| 6,743,222 B2 | 6/2004 | Durkin et al. | 606/9 |
| 6,749,624 B2 | 6/2004 | Knowlton | 607/104 |
| 6,758,845 B1 | 7/2004 | Weckwerth et al. | 606/9 |
| 6,878,144 B2 | 4/2005 | Altshuler et al. | 606/9 |
| 6,936,044 B2 | 8/2005 | McDaniel | 606/9 |
| 7,041,094 B2 * | 5/2006 | Connors et al. | 606/9 |
| 2003/0032950 A1 | 2/2003 | Altshuler et al. | 606/9 |
| 2003/0045916 A1 | 3/2003 | Anderson et al. | 607/89 |
| 2003/0055414 A1 | 3/2003 | Altshuler et al. | 606/9 |
| 2003/0065313 A1 | 4/2003 | Koop et al. | 606/9 |
| 2003/0199859 A1 | 10/2003 | Altshuler et al. | 606/9 |
| 2004/0024388 A1 | 2/2004 | Altshuler | 606/2 |

FOREIGN PATENT DOCUMENTS

| | | | |
|---|---|---|---|
| CA | 1041610 | 10/1978 | 326/16 |
| DE | 33 47 730 A1 | 7/1985 | |
| DE | 39 06 860 A1 | 9/1989 | |

| | | |
|---|---|---|
| EP | 0 565 331 A2 | 4/1993 |
| GB | 634113 | 3/1950 |
| GB | 2 360 946 A | 10/2001 |
| JP | 4-98795 | 3/1992 |
| WO | WO 86/02783 | 5/1986 |
| WO | WO 89/00871 | 2/1989 |
| WO | WO 95/15725 | 6/1995 |
| WO | WO 96/22813 | 8/1996 |
| WO | WO 97/37723 | 10/1997 |
| WO | WO 98/24514 | 6/1998 |
| WO | WO 98/38933 | 9/1998 |
| WO | WO 98/51235 | 11/1998 |
| WO | WO 99/07438 | 2/1999 |
| WO | WO 99/11324 | 3/1999 |
| WO | WO 00/54685 | 9/2000 |
| WO | WO 00/54685 A3 | 9/2000 |

OTHER PUBLICATIONS

Bartley et al., "An Experimental Study to Compare Methods of Eyelash Ablation," *Ophthalmology*, 94:1286-1289 (1987).
Boulnois, "Photophysical Processes in Recent Medical Laser Developments: a Review," *Lasers in Medical Science*, 1:47-64 (1986).
Finkelstein et al., "Epilation of Hair-Bearing Urethral Grafts Using the Neodymium:YAG Surgical Laser," *J. Urology*, 146:840-842 (1991).
Grossman et al., "Prospective Evaluation of the Argon Laser in the Treatment of Trichiasis," *Ophthalmic Surgery*, 23:183-187 (1992).
Grossman et al., "Experimental Comparison of Laser and CryoSurgical Cilia Destruction," *Ophthalmic Surgery*, 23: 179-182 (1992).
Kuriloff et al., "Pharyngoesophageal Hair Growth: the role of Laser Epilation," *Case Reports*, 98:342-345 (1988).
R.M. Adrian, "Treatment of Facial Telangiectasia Using the VersaPulse® Variable Pulse Width Frequency Doubled Neodymium:YAG Laser: A Case Report," 2 pages in length.
J.C. Allain et al., "Isometric Tensions Developed During the Hydrothermal Swelling of Rat Skin," *Connective Tissue Research*, vol. 7, pp. 127-133 (1980).
R.R. Anderson et al., *International Advances in Surgical Oncology (vol. 5)*, section entitled "Lasers in Dermatology Provide a Model for Exposing New Applications in Surgical Oncology," publisher Alan R. Liss, Inc. (1982), pp. 341-358.
R.R. Anderson, Brochure by Palomar Medical Technologies, Inc., "A Clinical Study on Ruby Lasers for Permanent Hair Reduction," 8 pages in length (1999).
R.R. Anderson, "Safety and Efficacy of the Palomar Ruby Laser for Hair Removal," Harvard Medical School, Mar. 1997, 2 pages in length.
R.R. Anderson, "Hair Removal Using Light," Harvard Medical School, Mar. 1997, 2 pages in length.
R.R. Anderson, "Clinical Use of the EpiLaser® System," 8 pages in length (1998).
Brochure, from Laser Aesthetics, Inc., "The Cool Touch Laser," one page in length.
C. Chess et al., "Cool Laser Optics Treatment of Large Telangiectasia of the Lower Extremities," *J. Dermatol. Surg. Oncol.*, vol. 19, pp. 74-80 (1993).
W.F. Coulson et al., "Nonablative Laser Treatment of Facial Rhytides: Animal Study," *Abstract of BIOS '98 Symposium [Cutaneous Applications of Lasers]*, Jan. 24-30, 1998 in San Jose, CA, one page in length.
C.C. Danielsen, "Age-related thermal stability and susceptibility to proteolysis of rat bone collagen," *Biochem J.*, vol. 272, No. 3, Dec. 15, 1990, pp. 697-701.
C.C. Danielsen, Thermal Stability of Reconstituted Collagen Fibrils, Shrinkage Characteristics upon In Vitro Maturation, *Mechanisms of Ageing and Development*, vol. 15, pp. 269-278 (1981).
J.S. Dover et al., "Pigmented Guinea Pig Skin Irradiated With Q-Switched Ruby Laser Pulses," *Arch. Dermatol.*, vol. 125, Jan. 1989, pp. 43-49.

R. Fitzpatrick, "Treatment of Wrinkles with the UltraPulse $CO_2$ Laser," 3 pages in length.
L. Goldman, "Comparison of the Biomedical Effects of the Exposure of Human Tissues to Low and High Energy Lasers," *Ann. N.Y. Acad. Sci.*, vol. 122, May 29, 1965, 1965, pp. 802-833.
"Laser Surgery of Angiomas with Special Reference to Port-Wine Angiomas," *AMA Association*, Jun. 18-22, 1967, 8 pages in length.
J.M. Grevelink et al., "Clinical and Histological Responses of Congenital Melanocytic Nevi After Single Treatment With Q-Switched Lasers," *Arch. Dermatol.*, vol. 133, Mar. 1997, pp. 349-353.
K. Kincade, "Demand for Laser Resurfacing Soars," *Dermatology Times*, vol. 16, No. 10, Oct. 1995, 4 pages in length.
P. Kronick et al., "The Locations of Collagens with Different Thermal Stabilities in Fibrils of Bovine Reticular Dermis," *Connective Tissue Research*, vol. 18, pp. 123-134 (1988).
H. Kubota et al., "Atrial Ablation With an IRK-151 Infrared Coagulator," *Ann. Thoracic Surg.*, vol. 66, pp. 95-100 (1998).
J.G. Kuhns et al., "Laser Injury in Skin," *Laboratory Investigations*, vol. 17, No. 1, pp. 1-13 (1967).
M.A. Mainster, "Ophthalmic applications of infrared lasers—thermal considerations," *Invest. Ophthalmal. Visual Sci.*, vol. 18, No. 4, Apr. 1979, pp. 414-420.
T. Matsumoto et al., "Ruby Laser Treatment of Melanin Pigmented Skin Lesions using Toshiba Model LRT—301 A Ruby Laser," *Journal of the Japanese Society for Laser Surgery and Medicine*, vol. 10, No. 3, Dec. 1989, pp. 451-454.
J.B. Murdoch, *Illumination Engineering—From Edison's Lamp to the Laser*, Chapt. 6.8 entitled "Tungsten-Halogen Lamps," published by Macmillan Publishing Company (1985), pp. 208-211.
M.H. Niemz, *Laser-Tissue Interactions Fundamentals and Applications*, Chapt. 3.2.3 entitled "Heat Effects," published by Springer-Verlag Berlin Heidelberg (1996), pp. 77-80.
T. Ohshiro et al., "The Ruby and Argon Lasers in the Treatment of Naevi," *Annals Academy of Medicine*, vol. 12, No. 2 (Suppl.), Apr. 1983, 8 pages in length.
T. Ohshiro, "Treatment by Ruby Laser Beams in the Field of Dermatology," "*Japan Medical News*," Separate Volume No. 2768, issued on May 14, 1997, 21 pages in length (English translation attached).
H. Ohtsuka et al., "Ru Laser Histological Studies and Clinical Experiences of Ruby Laser Treatment," 9 pages in length (1991) (1st page is an English Abstract).
I. Ono et al., "Histopathological Alteration of Skin and Irradiation of Rudy Laser," *Journal of the Japanese Society for Laser Surgery and Medicine*, vol. 11, No. 4, Mar. 4, 1991, 2 pages in length (1st page is an English abstract).
D.Y. Paithankar et al., "Acne Treatment With a 1,450 nm Wavelength Laser and Cryogen Spray Cooling," *Lasers in Surgery and Medicine*, vol. 31, pp. 106-114 (2002).
J.A. Pearce et al., "Kinetic Models of Laser-Tissue Fusion Processes," *Biomed. Sci. Instrum.*, vol. 29, pp. 355-360 (1993).
L.L. Polla et al., "Melanosomes Are a Primary Target of Q-Switched Ruby Laser Irradiation in Guinea Pig Skin," *The Journal of Investigative Dermatology*, vol. 89, No. 3, Sep. 1987, pp. 281-286.
Press Release, "New Laser Eliminates 'Lipstick Bleed,'" 3 pages in length.
Spectrum Medical Technologies, Inc., an operator's manual written by Lasermetrics, Inc., exclusively for Spectrum Medical Technologies, Inc., Q-Switched Ruby Laser System Model RD-1200, 23 pages in length.
E.R. Squibb & Sons, "Lasers Light the Way to New Research Concepts in Science Industry Medicine," 33 pages in length.
R. Tanino et al., "Development of Ruby Laser System for Medical Use," *Journal of the Japanese Society for Laser Surgery and Medicine*, vol. 11, No. 4, Mar. 4, 1991, pp. 93-98.
K. Iwasaki et al., (Astract) "Development of Laser Systems for Treatment of Hyperpigmented Skin Lesions," *Publication unknown—entire article is in Japanese except for the Abstract*, revised Mar. 1, 1989, pp. 26-34 (Abstract appears on page 34).

* cited by examiner

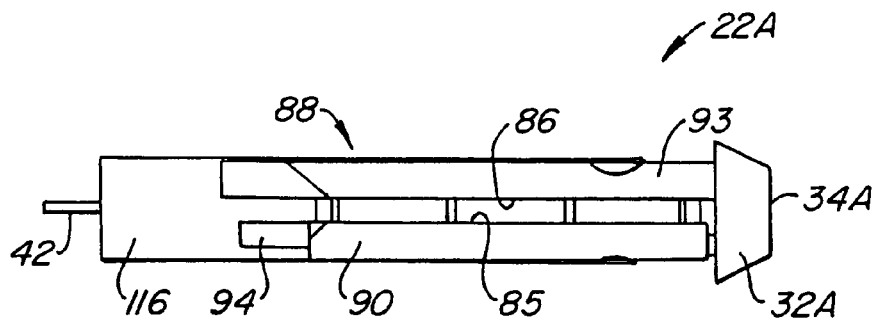
FIG. 8C.
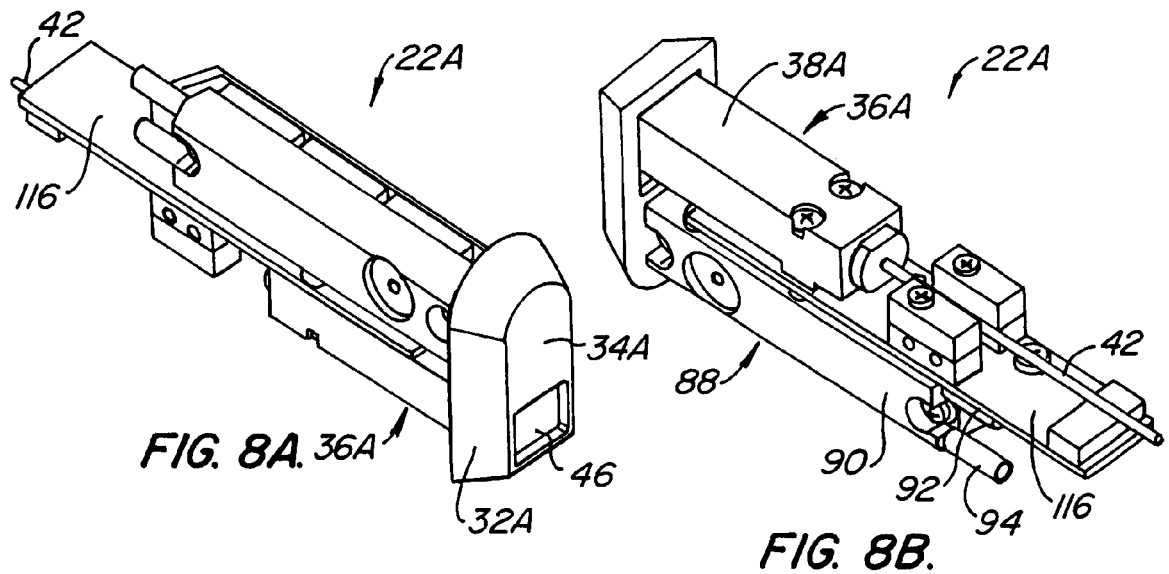
FIG. 8A.
FIG. 8B.
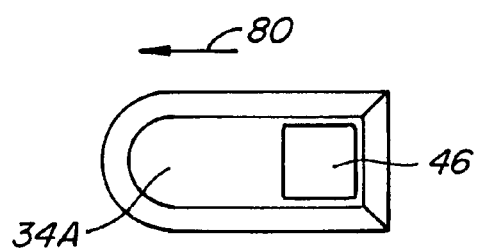
FIG. 8D.

| FIG. 11E(1) | FIG. 11E(2) |

FIG. 11E(1)

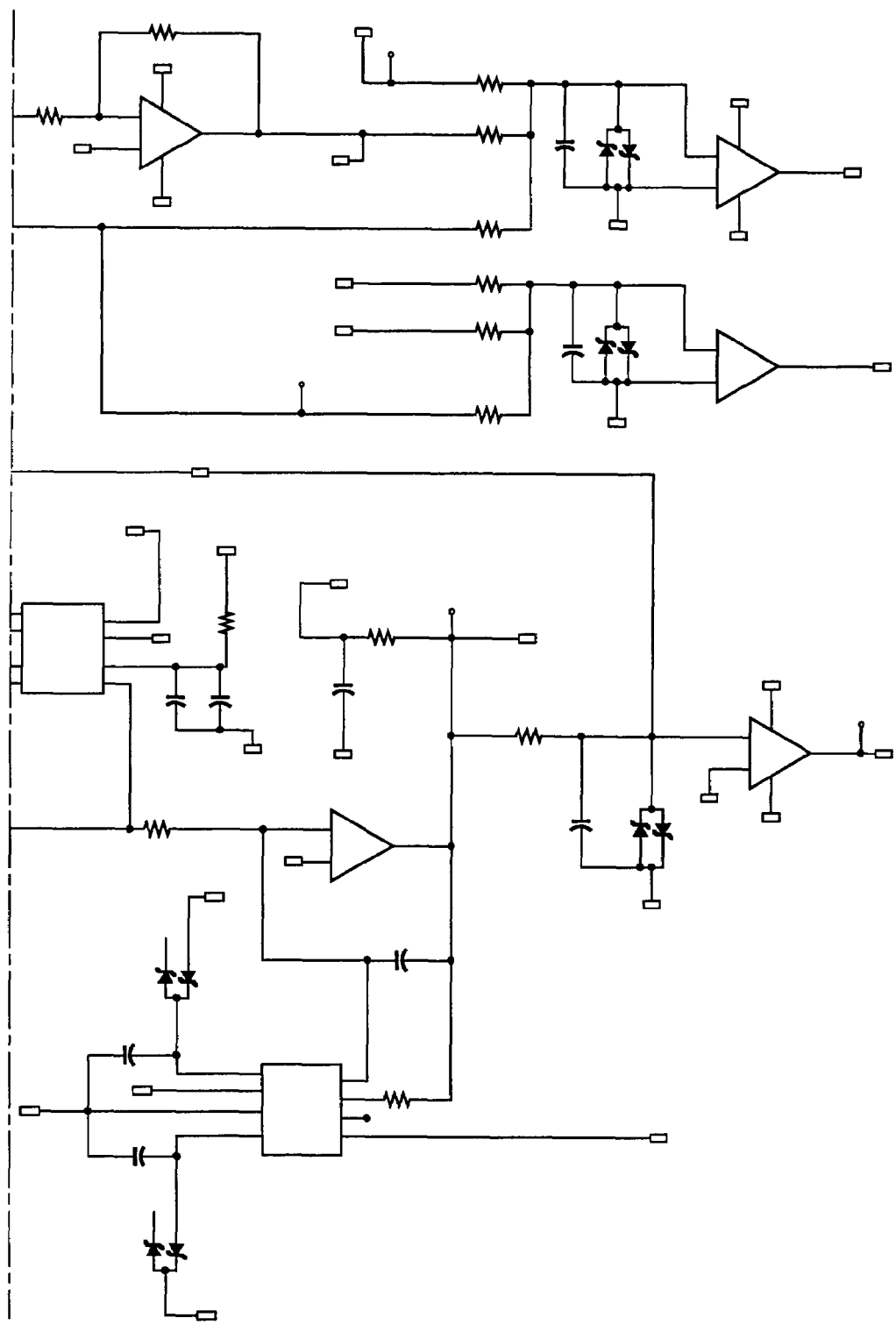
FIG. 11E(2)

HIGH VOLTAGE POWER SUPPLY CONTROL BOARD

| FIG. 11G(1) | FIG. 11G(2) |

FIG. 11G(1)

HIGH VOLTAGE POWER SUPPLY CONTROL BOARD
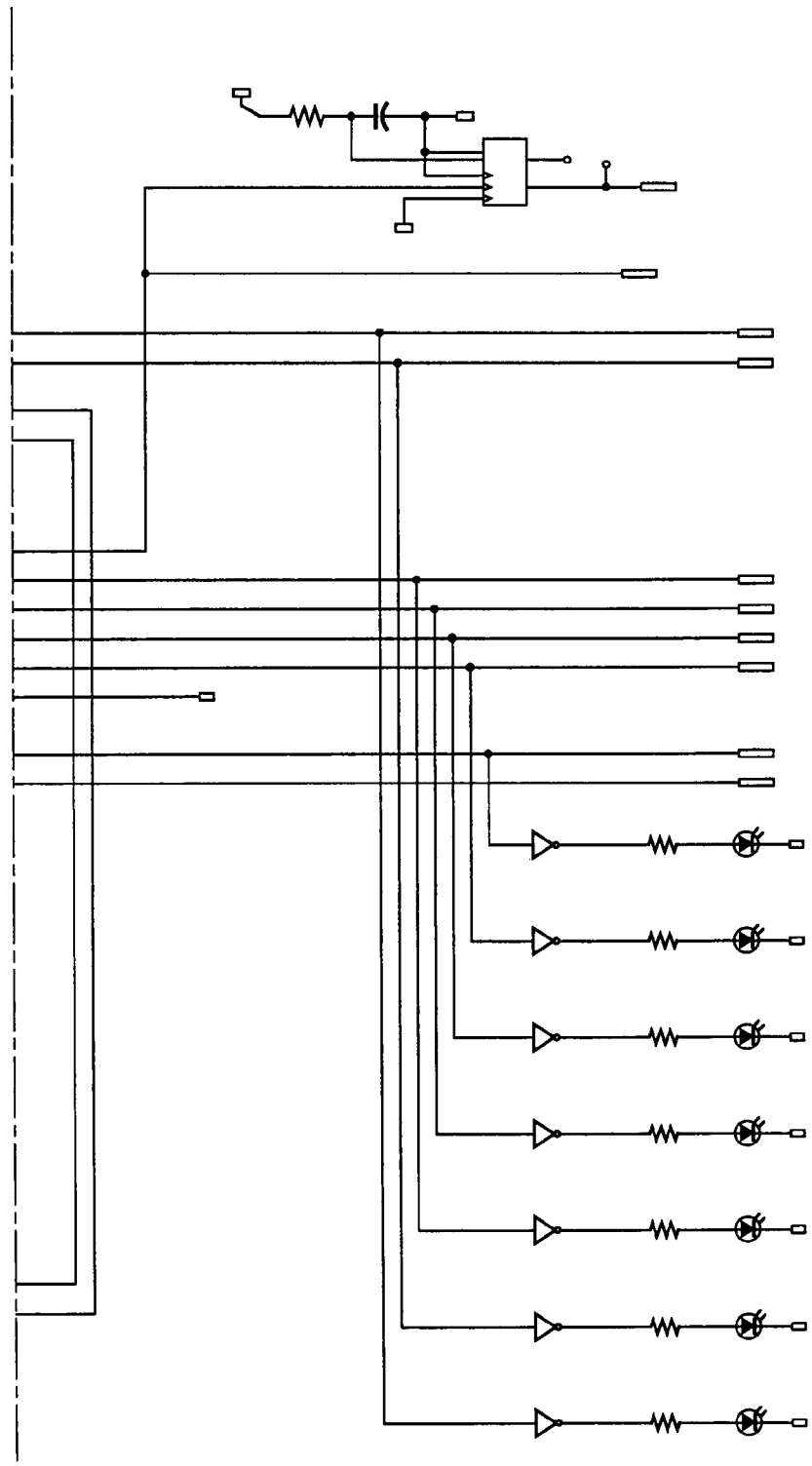
FIG. 11G(2)

TISSUE TREATMENT SYSTEM

PRIORITY INFORMATION

This application is a continuation of and claims priority from U.S. patent application Ser. No. 10/687,040, filed Oct. 16, 2003 now U.S. Pat. No. 7,041,094, which is a continuation of and claims priority from U.S. patent application Ser. No. 09/998,821, filed Nov. 15, 2001, now issued U.S. Pat. No. 6,666,856, which is a divisional of and claims priority from U.S. patent application Ser. No. 09/270,118, filed Mar. 15, 1999, now U.S. Pat. No. 6,383,176, which is related to a Provisional Patent Application Ser. No. 60/124,450, and Provisional Patent Application Ser. No. 60/124,709, both filed on Mar. 15, 1999, the disclosures of which are incorporated herein by reference.

BACKGROUND OF THE INVENTION

Use of light to denature very specific kinds of tissue has been called wavelength-selective photo-thermolysis. The use of lasers for this purpose has been well described in the literature. See, for example, R. G. Wheland, "Laser-assisted hair removal", Laser in Dermatology, Vol. 15, pp. 469-477, and references cited. By choosing a laser with the right wavelength and energy per unit area (fluence), a particular light-absorbing target substance (chromophore) in living tissue, such as melanin or hemoglobin, will absorb energy from the laser beam and become hot enough to destroy functionality in the tissue containing the chromophore. Tissue in the same area that does not have high concentration of the target chromophore will not be affected.

Hair includes two basic parts, the shaft, which is the portion of the hair above the epidermis, and the root, which is the portion below the surface of the epidermis. Various tissues surround the root of the hair. Hair color is primarily do to the presence of melanin in the hair. Melanin is created at the base of the hair follicle and is passed into the hair as it grows. The presence of melanin has made it possible to use lasers and other light sources for hair removal with melanin as the target chromophore. The hair follicle and surrounding structure (referred to collectively as hair tissue) are selectively heated when the melanin in the hair tissue and in the hair root itself and is exposed to treatment radiation. The hair tissue is thermally damaged so that a result of the localized heating, many of the exposed hairs later atrophy and are sloughed from the epidermis.

The early work in this field was centered around a wavelength with very high melanin absorption, the pulsed ruby laser (694 nm). Long pulse ruby lasers (as opposed to Q-switched ruby lasers) typically have a pulse duration in the 1 millisecond range. Although the wavelength is highly absorbed in melanin, the wavelength selection has significant limitations with darker skin types as the epidermis can blister from the superficial melanin heating.

Many different approaches to hair removal have been explored since the early ruby laser evaluation. A common trend is a continual shift towards longer wavelengths, which have less melanin absorption, as it allows treatment of patients with a darker range of skin tones. Initially, alexandrite (755 nm) was evaluated and later a diode approach (810 nm). The alexandrite laser offers improved clinical capabilities over the ruby laser if one considers treatment of darker skin types. However, from engineering and system performance measures, the two systems are similar in terms of size, utility requirement, treatment speed, and system cost. In contrast, the high pulse energy diode laser allows the system to be much smaller than previous systems with an ability to run off of standard power. One commercially-available system, sold by Coherent of Santa Clara as Lightsheer, weighs in the 45 kg (100 pound) range and allows the physician to treat the darkest skin types with minimal risk of post operative blistering. Unfortunately, the high pulse energy diode approach is very expensive as it requires up to 100 diode bars to achieve the peak powers needed for the desired clinical result. Another limitation with this approach is in the delivery device. The current Lightsheer system houses all diodes and associated hardware in a handpiece that is used in direct contact with the skin. This approach results in a heavy handpiece, weighing several pounds, that causes user fatigue and an overall bulky design.

Dermatologists have used cooling devices in dermatologic applications prior to laser treatment. The purpose is to chill the skin with the understanding that exposure to treatment radiation will elevate the epidermal temperature. Chilling lowers the initial temperature so that the post treatment temperature at the epidermis will not create a heat-induced blister. U.S. Pat. No. 5,735,844 describes apparatus which uses a cooled lens, through which radiation passes, pressed against the patient's skin to cool the epidermis.

SUMMARY OF THE INVENTION

The present invention is directed to a hair removal device and method by which hair tissue-damaging radiation passes from a radiation source through a recessed window to the patient's skin. The hair removal device also includes a skin-cooling element having a cooling surface which is used to contact the skin prior to exposure of that skin area to the radiation. The window is laterally offset from the cooling surface as well as spaced apart from the cooling surface in a direction away from the patient's skin so to create a gap between the window and the patient's skin.

The presence of a gap between the window of the radiation source and the patient's skin offers several benefits. One problem associated with a contact cooling window in direct contact with the skin is debris build up. Dermatologic tissue accumulates on the contact window as treatment pulses are delivered. The window must be periodically wiped in order to preserve the window from local, intense overheating that thermally and mechanically stresses the window and causes pitting. A recessed window does not exhibit this problem. Another advantage is that the window can be kept warm and above the local dewpoint temperature for both the inner and outer surfaces, so water and other condensables do not collect on it. Since the window is not in contact with the skin, it does not cause any re-heating of the pre-cooled skin.

In one embodiment of a hair removal device the radiation source includes an optical chamber having an exit aperture covered by the recessed window and an optical fiber entrance in which an optical fiber can be housed to permit tissue-damaging radiation to pass from the optical fiber into the optical chamber. The optical chamber may also be heated to help prevent condensation from forming on the walls of the chamber or the window. The window may include both an inner window and an outer, user-replaceable window; if the outer window becomes damaged through use, it can be easily replaced without affecting the integrity of the optical chamber. This is an advantage over fixed, single window designs that are rendered unusable if there is a surface imperfection due to, for example, localized pitting.

The hair removal device may be coupled to a laser which supplies laser light to the radiation source for passage through the recessed window. The laser may be controlled by useroperated laser power inputs including a laser-pulse duration input and one of a laser-pulse amplitude input and a laser-pulse fluence input. The laser-pulse duration input may be adjusted according to the diameter of the hair, which corresponds to the thermal relaxation time of the hair. Therefore, smaller diameter hairs will typically call for shorter laser-pulse duration inputs while larger diameter hairs will call for a longer laser-pulse duration inputs. Although larger diameter hairs will be selectively heated with short pulses, defined as a pulse duration shorter than the thermal relaxation time of hair, the peak power on the epidermis is unnecessarily higher than it needs to be. This can result in a heat-induced blister.

Another aspect of the invention relates to a method for removing hair including the steps of (1) determining the diameter typical of the hair to be removed, (2) selecting a laser-pulse duration for a hair removal device according to this diameter of the hair so that smaller diameter hair results in a shorter laser-pulse duration than larger diameter hair, and (3) applying laser energy through a window of a hair removal device of the selected laser-pulse duration to a patient's skin to cause thermal injury to hair tissue. This applies to both individual hairs and a plurality of hairs.

The method may include selecting a chosen one of a laser-pulse amplitude and a laser-pulse fluence prior to the applying step. Further, the method may also include positioning a cooling element of the hair removal device against a first target area and then moving, after a period of time, the cooling element from the first target area to a second target area so that the window overlies and is spaced apart from the first target area; laser energy is then applied to the first target area through the window with the window overlying and spaced apart from the first target area.

The pulse duration has been shown to have significant clinical implications. A short pulse, typically in the sub-5 ms, range creates high peak powers because high fluence is required to deliver enough energy to achieve the proper clinical endpoint. High peak power tends to heat the epidermis. Longer pulses result in lower peak power.

Shorter wavelengths, such as 694 nm, do not penetrate deeply into the patient's skin so, some believe, that it may be desirable, with such shorter wavelengths, to use a convex window pressing against the skin to shorten the path from the window to the hair tissue as is taught by U.S. Pat. No. 5,735,844 patent. It has been found that by the use of longer wavelengths which are still absorbed by melanin, such as 800 to 1200 nm, it is not necessary for the window of the radiation source to press against the patient's skin to effectively irradiate the hair tissue at a target area.

Another aspect of the invention is the recognition that it is not necessary to cool the skin the same time it is being irradiated. This is because once the skin has been cooled through contact with a cold surface, removal of the cold surface permits the skin to warm up but it does so much more slowly than it has cooled down because it is relying almost entirely on convection rather than conduction. Recognizing the fact that the skin remains sufficiently cool for a second or two after removal of the cooling surface permits the window of the radiation source to be positioned spaced apart from the surface of the skin. This eliminates some problems created when the window of the radiation source directly contacts the skin during irradiation, such as window surface damage caused by intense heating from hair fragments that are heated by the laser beam.

A further aspect of the invention is the recognition that radiation in the longer wavelengths (about 800 to 1200 nm) of the band of melanin-absorbing radiation, typically considered from about 600 nm to 1200 nm, can be used without the need for the use of chromophore contaminants as taught by U.S. Pat. No. 5,425,728.

Other features and advantages of the invention will appear from the following description in which the preferred embodiments have been set forth in detail in conjunction with the accompanying drawings.

BRIEF DESCRIPTION OF THE DRAWINGS

FIGS. 8A, 8B, 8C and 8D are two isometric views, a top plan view and an end view of another alternative embodiment of the hair removal device of FIG. 3A with the ergonomically shaped body removed;

DESCRIPTION OF THE SPECIFIC EMBODIMENTS

Figure 1:
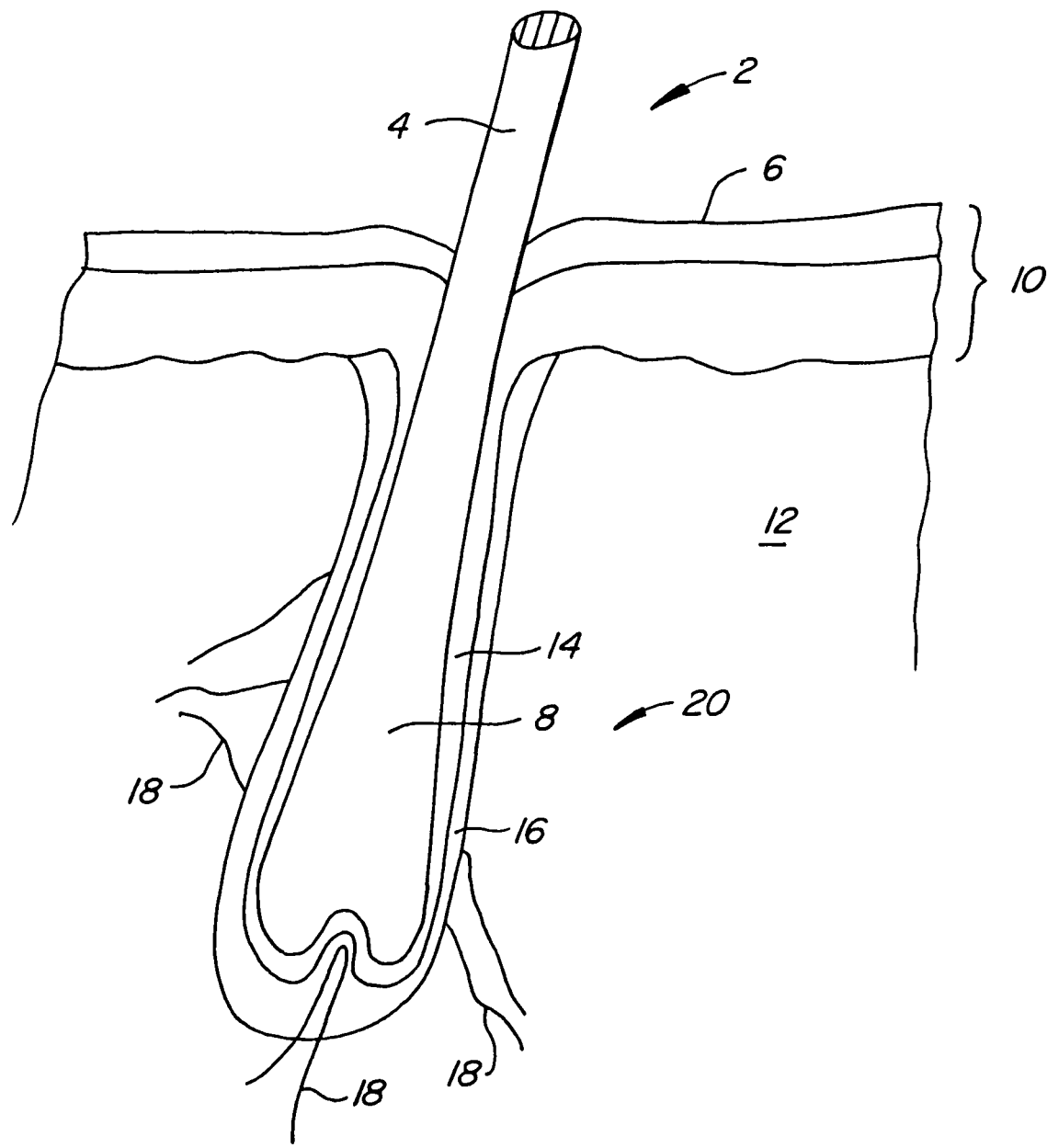
FIG. 1 is a simplified cross-sectional view of a hair with its root within a hair follicle.
Figure 2:
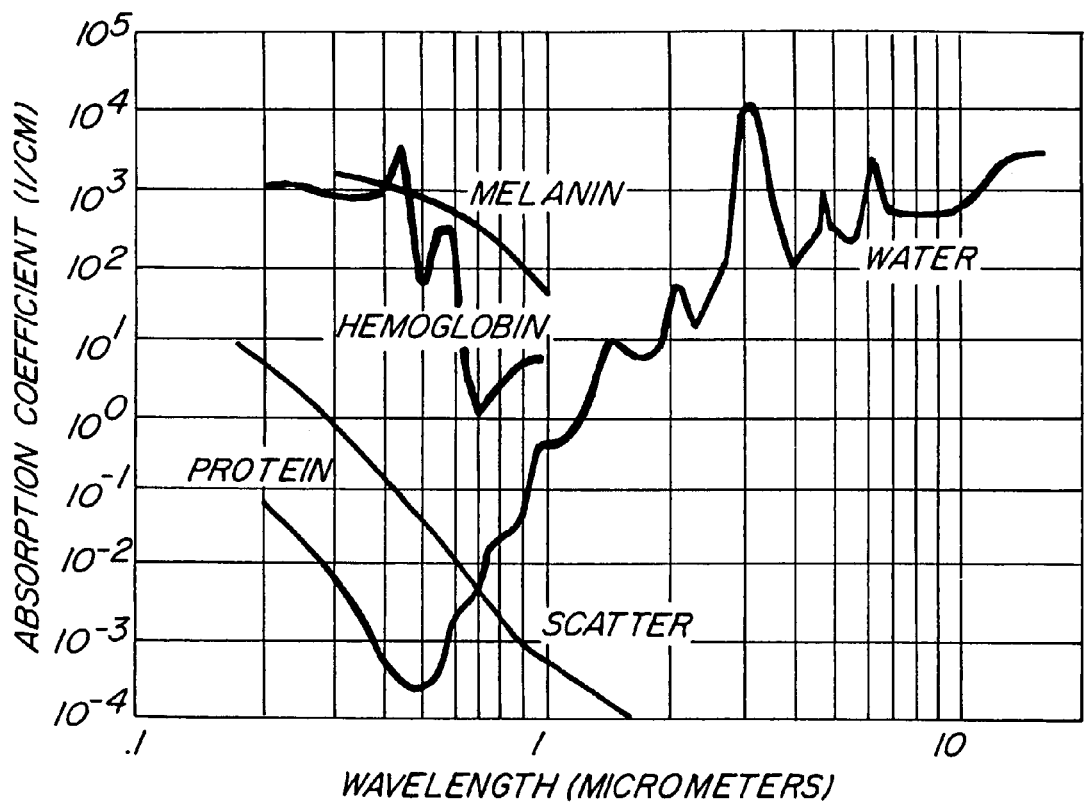
FIG. 2 plots absorption coefficient versus wavelength for different substances including melanin.

FIG. 1 illustrates, in simplified form, a hair 2 including a shaft 4 extending above skin surface 6 and a root 8 extending below the skin surface. The root 8 passes through epidermis 10 into dermis 12 with the base of the root being about 4 mm below surface 6. Root 8 is housed within hair follicle 14, hair follicle 14 being surrounded by various tissues including connective tissue sheath 16 and blood vessels 18. The various tissues closely surrounding root 8 and connected with the growth of hair 2, including hair follicle 14 and connective tissue sheath 16, are collectively referred to as hair tissue 20 in this application.

Because melanin is also present in epidermis 10, with darker skin types having more melanin than lighter skin types, it is important that the wavelength be long enough so that absorption is low for the moderate concentrations in melanin in the epidermis to permit most of the light to pass through to the root 8 and hair tissue 20 where melanin concentrations are relatively high compared to the epidermis. Therefore, it is preferred to use wavelengths in the 800 to 1200 nm range; in particular, an Nd:YAG (neodimium-doped YAG) laser having a wavelength of 1.06 micron is preferred because it is a relatively efficient source and the technology is well developed and readily available.

Figure 3:
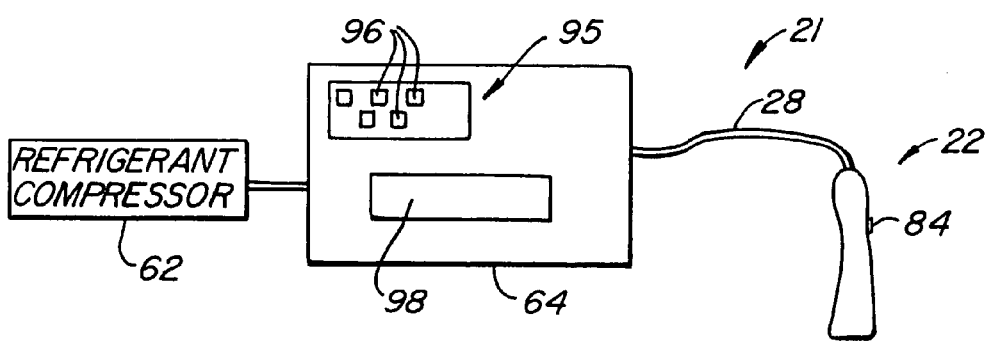
FIG. 3 is a schematic representation of a hair removal assembly made according to the invention.
Figures 3A, 3B, 4, 4A:
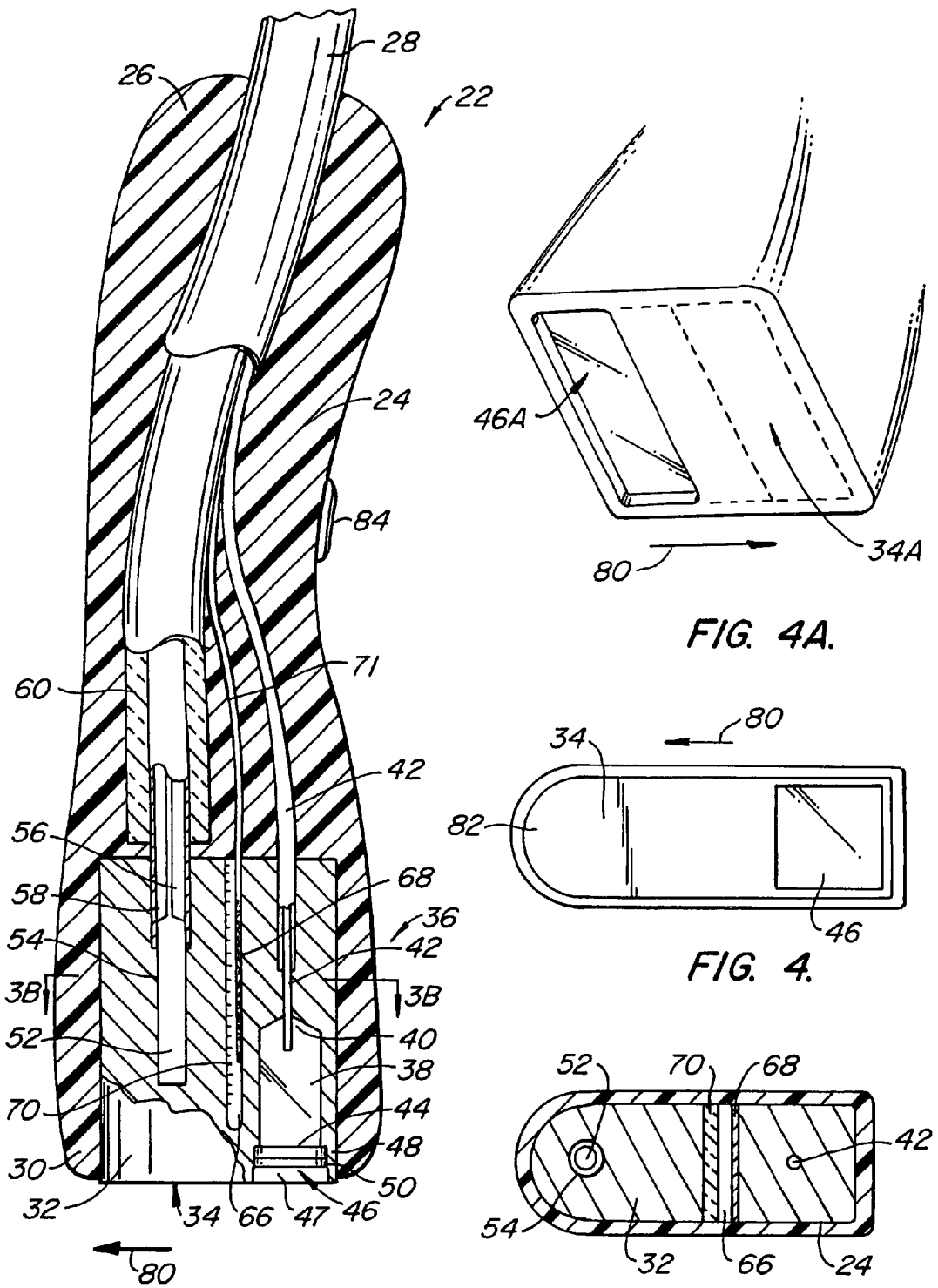
FIG. 3A is a simplified side view of the hair removal device of FIG. 3 with portions broken away to show internal detail.
FIG. 3B is a simplified cross-sectional view taken along line 3B-3B of FIG. 3A.
FIG. 4 is a bottom plan view of the hair removal device of FIG. 3A.
FIG. 4A is an overall view of the lower end of an alternative embodiment of the hair removal device of FIG. 3A.

FIG. 3 illustrates, schematically, a hair removal assembly 21 including a hand-held hair removal device 22, device 22 shown in more detail in the simplified views of FIGS. 3A and 3B. Device 22 includes a hand-grippable body 24 having an upper or outer end 26 into which an umbilical cable 28 passes. Body 24 also has a lower or skin contacting end 30 housing a formed aluminum block 32, block 32 having various cavities to provide various features and functions as described below. Block 32 defines a cooling surface 34, see also FIG. 4, which is used to contact the patient's skin and cool the skin and prior to irradiation. Surface 34 is a low friction, high lubricity surface to help prevent bonding between the cooling surface and the skin.

Aluminum block 32 also houses a radiation source 36. Radiation source 36 includes a reflective chamber 38, in this embodiment having a square cross-sectional shape. Reflective chamber 38 has its walls covered with a highly reflective material, such as gold; the material is chosen for its reflective qualities for the particular wavelength radiation to be used. Other materials, such as dielectric layers combined with high-reflectivity metals, could also be used. Chamber 38 has an optical fiber entrance 40 to permit an optical fiber 42, or a bundle of optical fibers, to extend into chamber 38. The opposite end of chamber 38 has an exit aperture 44 covered by a recessed window 46. Recessed window 46 is spaced apart from cooling surface 34 by a distance or gap 47, such as about 1 to 3 mm (0.04 to 0.12 in). Recessed window 46 includes an inner window 48, typically permanently or semi-permanently mounted to aluminum block 32 at exit aperture 44, and an outer window 50. Outer window 50 is removable secured in place by the use of an clip, not shown, or other suitable means. Windows 48, 50 are made of a suitable material, such as fused silica, although other materials, such as optical glasses, could also be used. By the use of inner and outer windows 48, 50, if outer window 50 is damaged, it can be easily replaced by the user. Accordingly, outer window 50 acts as a sacrificial window which if damaged, such as can occur through spalling as a result of bits of hair exploding when subjected to high power radiation, can be easily replaced.

Cooling surface 34 is cooled through the use of a coolant evaporator 52 house within a blind bore 54 formed in aluminum block 30. The coolant, which may be of various commercially available types, commonly Freon® or other fluorinated hydrocarbons, is directed to evaporator 52 through a coolant liquid line 56 and is recycled back to a refrigerant compressor 62 through a coolant vapor return line 58. Line 58 coaxially houses coolant liquid line 56, line 58 being housed within thermal insulation 60. Lines 56, 58 and insulation 60 pass through umbilical cable 28 to refrigerant compressor 62 associated with a control console 64. Alternatively, cooling surface 34 can be cooled by a thermoelectric, Peltier device instead of the coolant evaporator. This, currently preferred, embodiment of the cooling device is discussed below with reference to FIGS. 8A-8D.

While it is desired to cool surface 34, such cooling can result in condensation on the surfaces of radiation source 36, in particular on the walls of chamber 38 and on recessed window 46. To help prevent this, a separation slot 66 is made between that portion aluminum block 32 used to cool surface 34 and that portion of the block used for radiation source 36. An electrical, typically resistive, heating element 68 is positioned along one wall of slot 66, the right wall as shown in FIGS. 3A and 3B, while the other, left wall is covered with thermal insulation 70. Heating element 68 is connected to console 64 through a conductor 71 extending along umbilical cable 28. In lieu of resistive heating element 68, the hot side of a thermoelectric type of heating element, such as discussed below with reference to FIGS. 8A-8D, could be used.

Laser hair removal treatments are designed to be effective and yet safe. That is, the treatment should cause thermal damage to hair tissue 20 but not substantial damage to surrounding tissue, such as blistering to the skin. To do so the energy per unit area (fluence) of the laser beam 74 at skin surface 6 must be controlled. Part of this control requires that the distance between skin surface 6 and the end of optical fiber 42 be controlled because beam 74 expands as it passes through reflective chamber 38. The distribution of energy across the laser beam at the skin surface should be substantially constant so that no hot spots, which could cause local damage to the epidermis, are created. Also, the individual exposure sites must fit tightly together, commonly called a tiled effect, so that there is little or no overlapping of the exposure sites and, at the same time, little or no area is left unexposed. The simplest shape that meets this tiling requirement is a rectangle. Other shapes can create a tiled pattern but they have other drawbacks. Reflective chamber 38 and window 46 both have square cross-sectional shapes for efficient and effective treatment.

Figure 5:
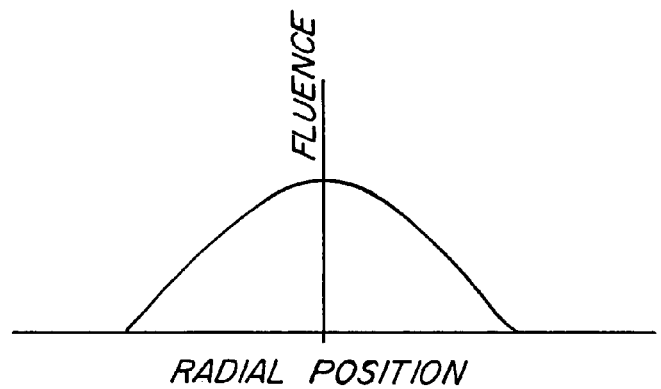
FIG. 5 is a theoretical plot of fluence versus radial position for a diverging beam.
Figure 5A:
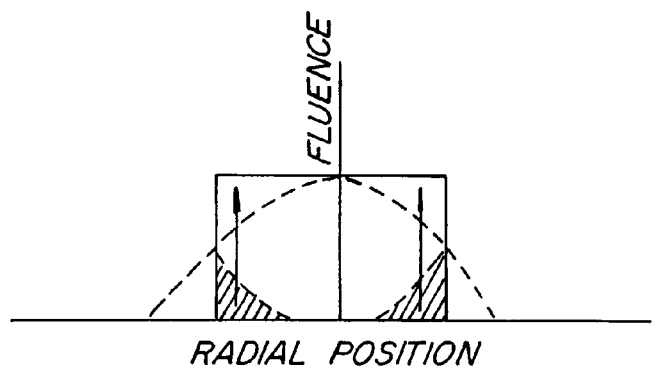
FIG. 5A shows an idealized plot of how to square off or equalize the fluence of the beam of FIG. 5.
Figure 6:
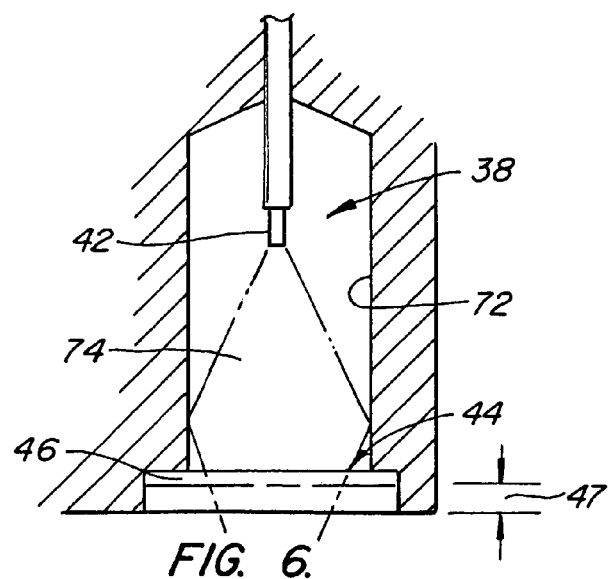
FIG. 6 is a simplified view of the radiation source of FIG. 3 showing how radiation is reflected from the walls of the reflective chamber to help equalize radiation intensity and reduce hot spots.

FIG. 5 illustrates a graph of fluence versus radial position for a diverging beam, such as from optical fiber 42. What is desired is to square off the graph to equalize the fluence over the beam spot. This is suggested in FIG. 5A in which those portions of the beam at the edges are reflected or folded over back into the main portion of the beam to create a generally square wave graph of fluence versus radial position. FIG. 6 illustrates how this is accomplished with the present invention. The walls 72 of chamber 38 are made to be highly reflective of the particular wavelength of radiation. In the preferred embodiment the wavelength is 1.06 micron and surface 72 is provided with a highly reflective gold surface. As suggested in FIGS. 5A and 6, the diverging laser beam 74 not only passes directly through window 46 but the edge portions of the beam are reflected off the walls 72 back into the main portion of the beam to create a generally equalized fluence level. Other optical arrangements can be used to help equalize the fluence applied to skin surface 6. For example, various devices called optical integrators or beam homogenizers are well known in the art of laser material processing. The simplicity of the present device is possible because the exit aperture, by virtue of being close to the cooling surface 34, is located close to the target surface.

Figure 9:
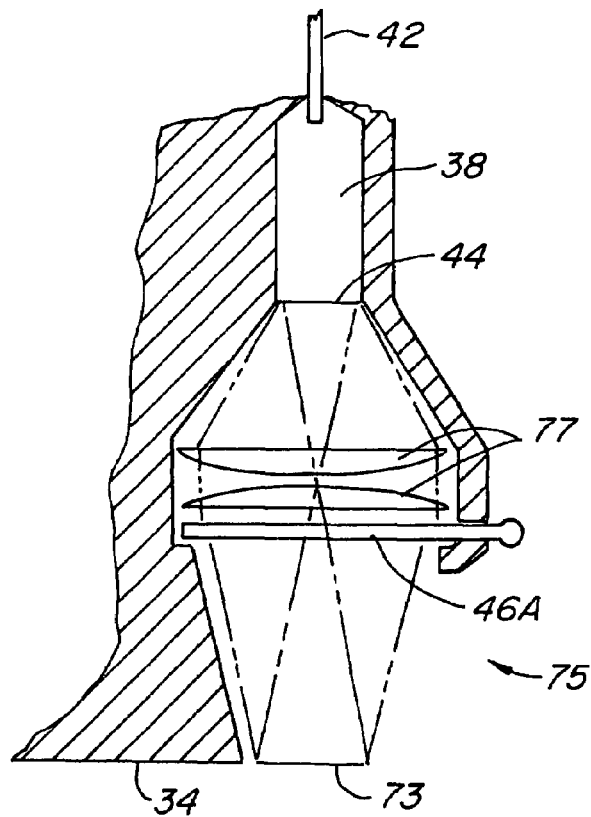
FIG. 9 is a simplified partial cross-sectional view of an alternative embodiment of the hair removal device of FIG. 3A in which the device is configured to permit the user to see the skin area being treated.

In another embodiment, shown in FIG. 9, reflective chamber 38, exit aperture 44 and protective window 46A are spaced much further from the skin surface to, for example, give the practitioner a better view of the treatment area 73 through a view port 75. View port 75 may be an open region, as illustrated, or it could include, for example, transparent and/or reflective members to permit direct or indirect viewing of area 73. In this case, a lens system 77 is used between exit aperture 44 and window 46A to make an image of the exit aperture on the skin surface at treatment area 73. With this approach, the size of the exit aperture need not be the same size as the treatment area 73 on the skin surface. The size of treatment area 73 could be made variable by proper selection of the focal length of lens system 77 and the distance between exit aperture 44 and the lens system. This would be useful when it is desired to use the device for other treatments, such as the treatment of varicose veins.

Figure 7:
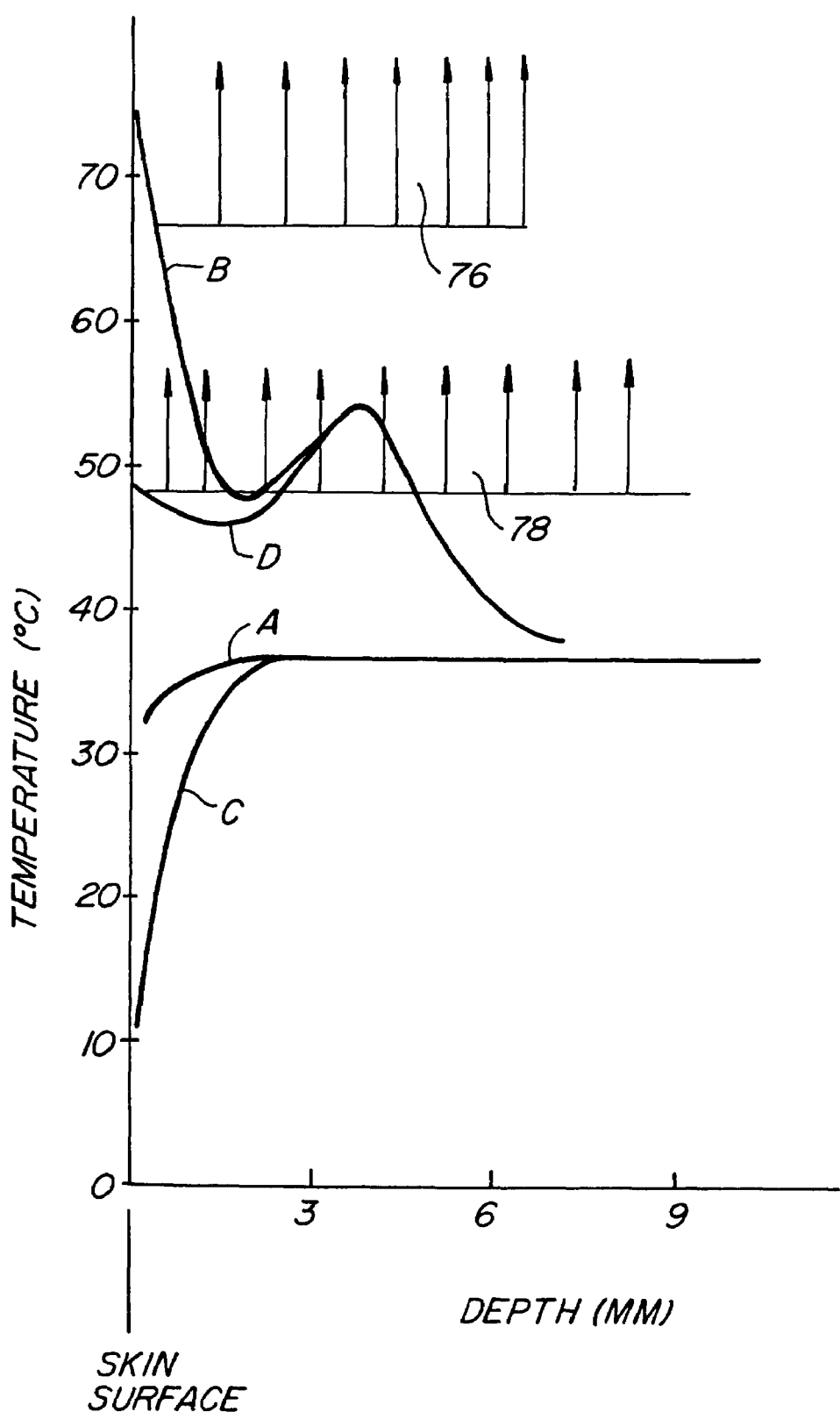
FIG. 7 shows several idealized plots of temperature versus depth below the skin surface.

One way to control unwanted thermal damage to the skin is to cool the epidermis. FIG. 7 illustrates several idealized plots of tissue temperature versus depth below the skin surface. Plot A shows the normal variation of temperature versus depth with the temperature rapidly approaching the normal core temperature of 37° C. Plot B illustrates the temperature at a range of tissue depth following a laser pulse when there has been no prior cooling of the skin. Assuming the energy is high enough to cause thermal damage at a depth of about 2 to 4 mm, the typical range of depths need to cause damage to hair tissue 20, the skin surface temperature is hot enough to cause blistering and burning. The blistering and burning range is indicated by region 76, that is above about 68° C., while the temperature needed to cause hair tissue damage is indicated by region 78, that is above about 48° C. Plot C illustrates the result of cooling the skin surface after adequate pre-cooling. Adequate pre-cooling has commonly been found to be created when an aluminum heat sink, pre-cooled to about 0° C., is applied to the skin surface for about 1 to 2 seconds. Plot D plots temperature versus skin depth immediately after exposing the skin surface, pre-cooled as in the Plot C, to a laser-pulse similar to that which created Plot B. As can be seen, pre-cooling the skin surface results in prevention of burning or blistering the skin while permitting the target tissue, that is hair tissue 20, to be raised to a sufficiently high temperature to cause thermal damage to the tissue. Note that the plots in FIG. 7 are not taken from actual test data but are idealized plots provided to aid understanding the advantages of pre-cooling of the skin.

Several patents discuss surface cooling to prevent tissue damage. See, for example, U.S. Pat. Nos. 5,057,104; 5,282,789 and 5,735,844. Coherent of Santa Clara, Calif. sells a diode laser system for dermatological use as the LightSheer. This product provides a hand piece with a cold window through which the laser exposure occurs. To use the device the window is first pressed against the treatment side for a period of time and then the laser beam is fired through the window. One of the problems with this simultaneous cooling technique when applied to laser hair removal is that it takes two to three seconds with the skin in contact with the cooled window to properly cool the skin surface to about 10 to 15° C. Thus, the practitioner must wait for about 2 to 3 seconds at each treatment site before firing the laser-pulse.

The present invention eliminates any need to wait prior to firing the laser-pulse by separating the cooling surface and the laser discharge window. As seen in FIG. 4, cooling surface 34 lies adjacent to window 46 in the direction of movement indicated by arrow 80. The width of surface 34 and window 46 are substantially the same while the length of 34 is about twice the length of window 46, that is with the length considered to be in the direction of arrow 80. Assuming a cooling time of 2 seconds is desired, the forward end 82 of cooling surface 34 is placed over the first target area on skin surface 6. After about one second in that position, device 22 is moved in the direction of arrow 80 the length of recessed window 46; in the preferred embodiment this is about one centimeter. At this time the first target area shifts to a position covered by cooling surface 34 but adjacent to window 46. After a second one-second interval, device 22 is again moved the length of recessed window 46; at this time the first target area, which has been cooled for a total of about two seconds, is aligned with recessed window 46. The practitioner then presses a fire button 84 on body 24 of device 22 causing a laser-pulse to be directed at skin surface 6. The practitioner then continues moving device 22 and pressing fire button 84 at one-second intervals to provide the desired laser treatment of the skin surface.

The desired two-second cooling of skin surface 6 could also be done with cooling surface 34 about the same size as window 46. To do so would require that device 22 be moved only every two seconds, or some other length of time needed to cool the skin surface 4. By making cooling surface 34 with a length greater than the length of window 46, the amount of time between laser-pulses need not be controlled by how long it takes to cool the skin surface. Rather, the device can be designed so that the time between laser-pulses is chosen to be at a comfortable pace for the operator while not unduly extending the time the entire procedure takes. For example, if it is believed that the proper interval between pulses is three-quarters of a second but the skin area needs to be cooled for three seconds, the length of cooling surface 34 could be made to be about four times the length of window 46; using these parameters, moving device 22 by the length of window 46 between each pulse permits the skin surface to be cooled for the desired three seconds while the practitioner can operate the fire button at the desired three-quarter second between pulses. Therefore, the length of the cooling surface (Y) is equal to the length of the window (X) multiplied by the time desired to cool the target site (C), the result divided by the desired interval between laser pulses (Z); that is, $Y=(X \times C)/Z$. Adjustments to the thermal capacity, thermal conductivity and temperature of block 30 and cooling surface 32 can also be made to vary the required time needed to cool skin surface 6.

FIG. 4A illustrates an alternative embodiment of the invention in which window 46A is rectangular having a width about three times its length. In this case cooling surface 34A would have a width about equal to the width window 46A. However, the length of cooling surface 34A is, like in the embodiment of FIG. 4, about twice the length of window 46A based on the premise that the interval between actuation of fire button 84 will be equal to one-half the length of time it is desired to apply equal surface 34A to the skin surface to properly cool the skin surface.

The pre-cooling of the skin surface followed by the irradiation is based on the premise that the skin can be cooled relatively quickly compared with the time it takes to warm back to its normal temperature. For example, using a cooling surface 34 maintained at about 0° C. and applying the cooling surface to skin surface 6 for one second lowers the skin surface temperature about 12° C.; application for two seconds lowers the skin temperature by about 18° C.; application for three seconds lowers the skin temperature by about 20° C. Therefore, two seconds of cooling time appears to be adequate with this particular cooling surface; three seconds of cooling time is better but only marginally so. While one second of cooling time does produce a significant drop in skin temperature, it may not be adequate depending upon various factors, primarily the amount of pigment in the patient's skin, the patient's hair color and other such factors. Accordingly, it is believed cooling times from about one to two seconds, and generally more preferably about two seconds, are expected to produce good results at a reasonable pace with the disclosed embodiment.

In another mode of operation which could be used by experienced practitioners, the laser system would be set to emit pulses continuously at a constant repetition rate of, for example, 1 Hz. The practitioner would hold the handpiece in continuous contact with the patient's skin and move it at a constant velocity equal to the product of exposure-area length time repetition rate. This will maximize the rate at which the treatment proceeds while still providing adequate skin cooling and complete coverage.

FIGS. 8A-8D illustrate another alternative embodiment hair removal device 22 but with the ergonomically shaped body shown in FIG. 3 removed. Device 22A is similar to device 22 but instead of using coolant evaporator 52, device 22 uses a thermoelectric device 88, typically a Peltier device. Thermoelectric device 88 has a warm part and a cold part created by the passage of electricity through the thermoelectric device. To remove the heat created, thermoelectric device 88 includes a water cooled heat sink 90 having inlet and outlet lines 92, 94. The cold part of device 88 is thermally coupled to aluminum block 32A so to cool cooling surface 34A.

Figure 10:
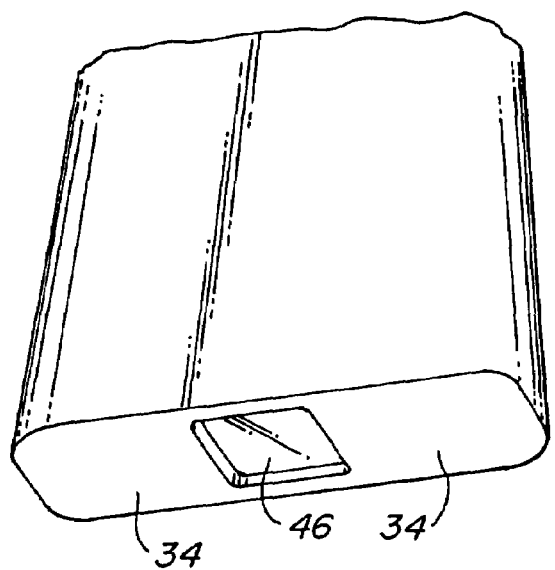
FIG. 10 is a simplified view of the bottom of a further alternative embodiment of the hair removal device of FIG. 3A showing leading and trailing cooling surfaces.
Figure 11A:
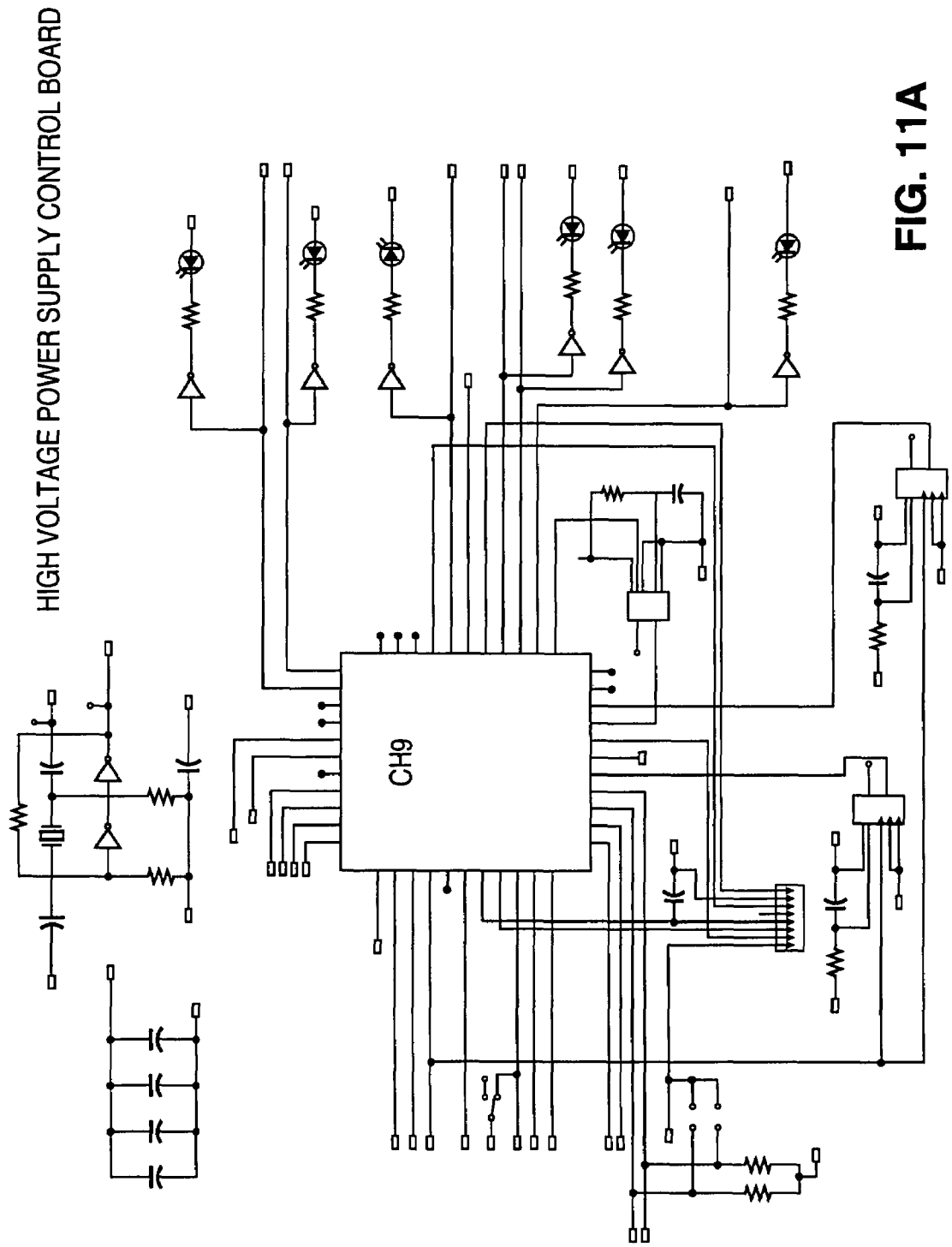
FIGS. 11A-11K show an embodiment of a power supply for driving a flash lamp herein.
Figure 11B:
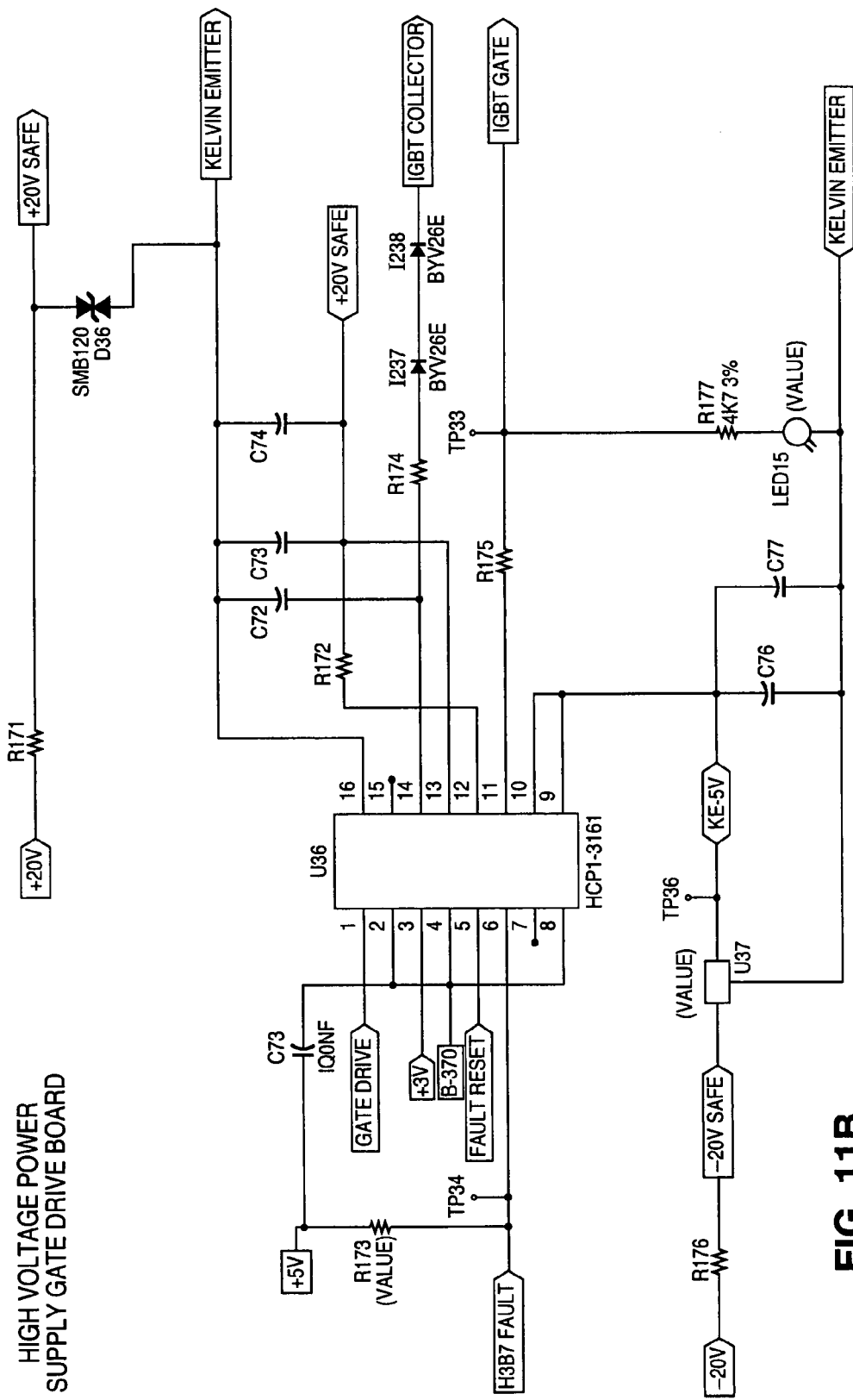
Figure 11C:
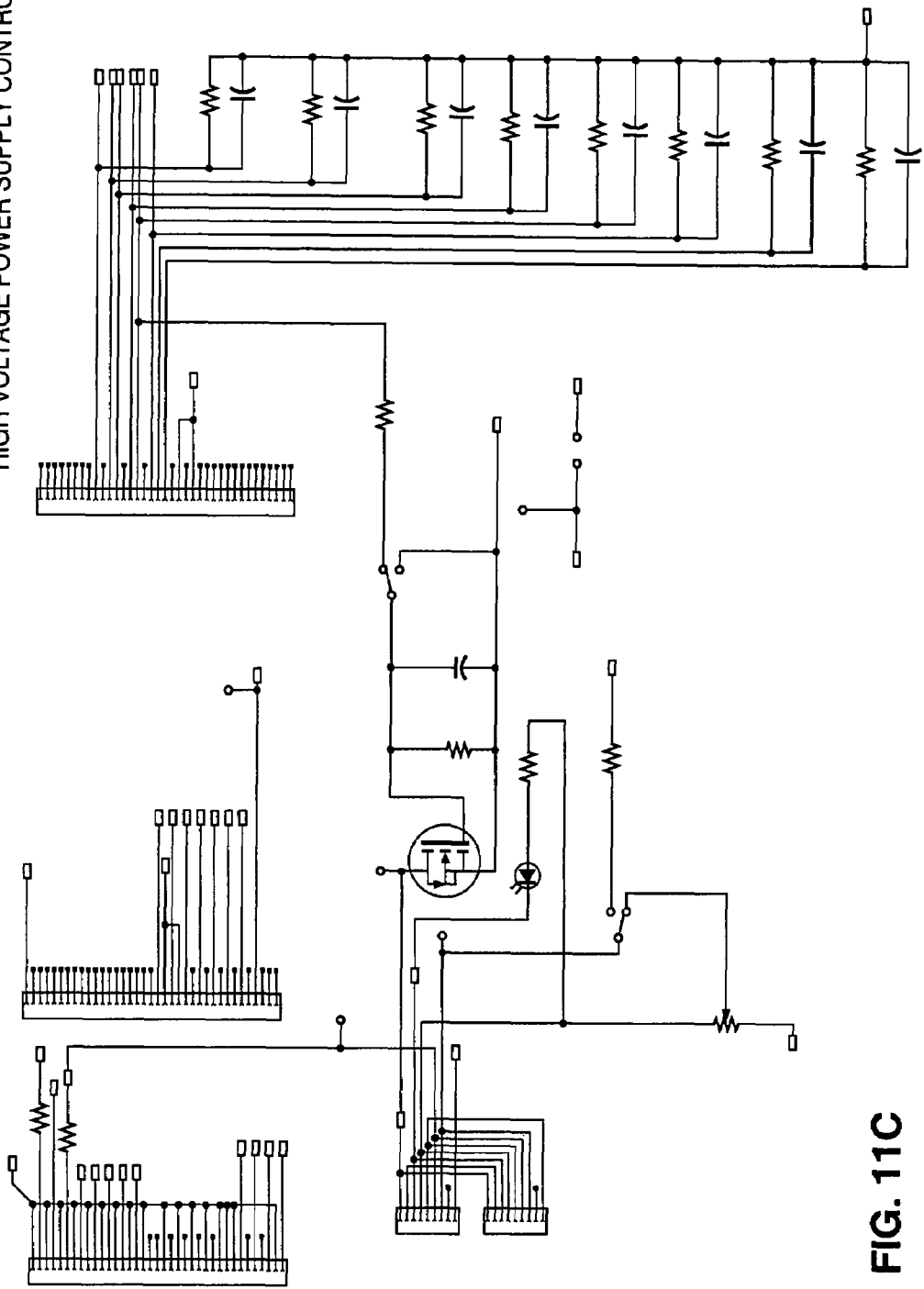
Figure 11D:
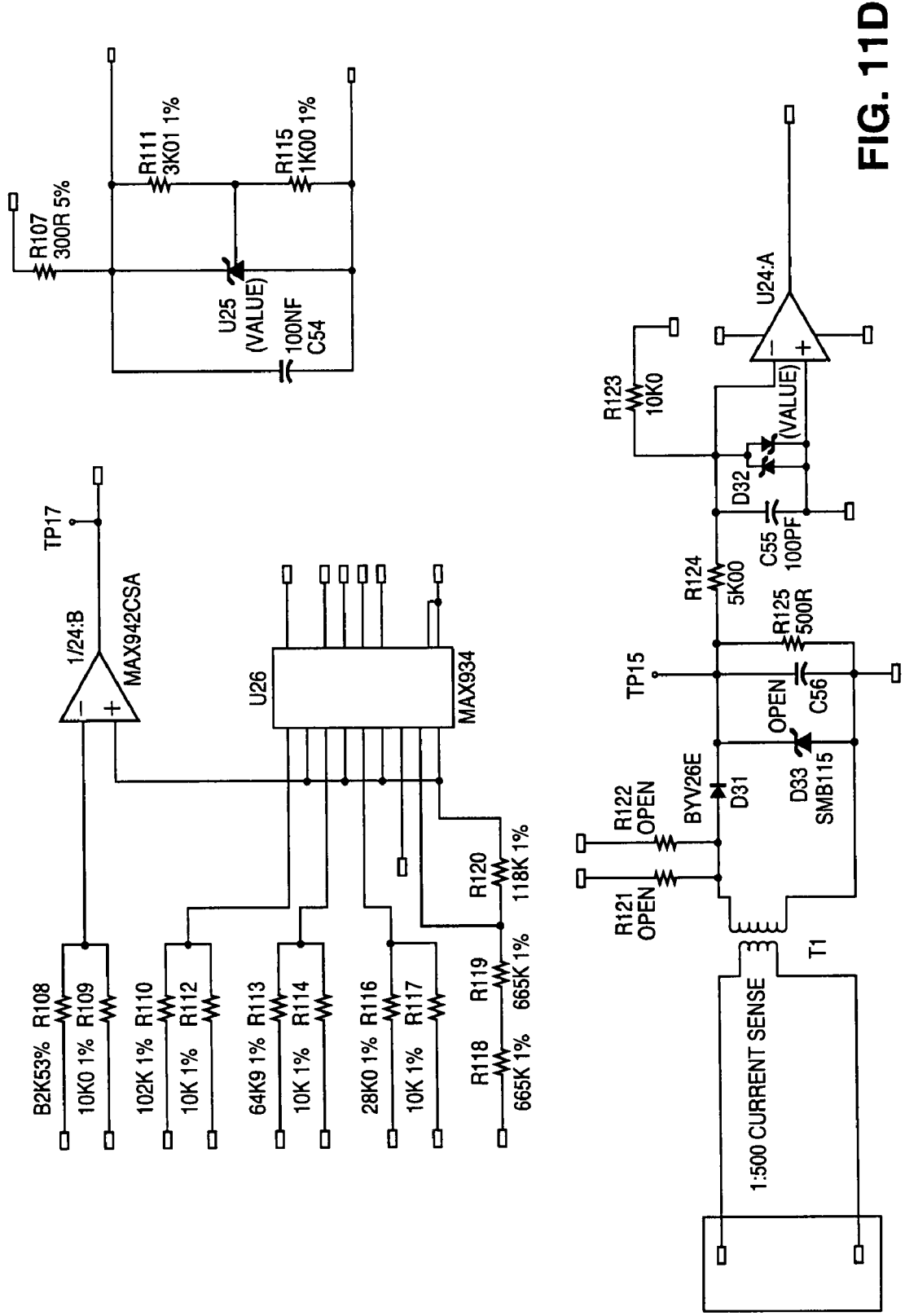
Figure 11E:
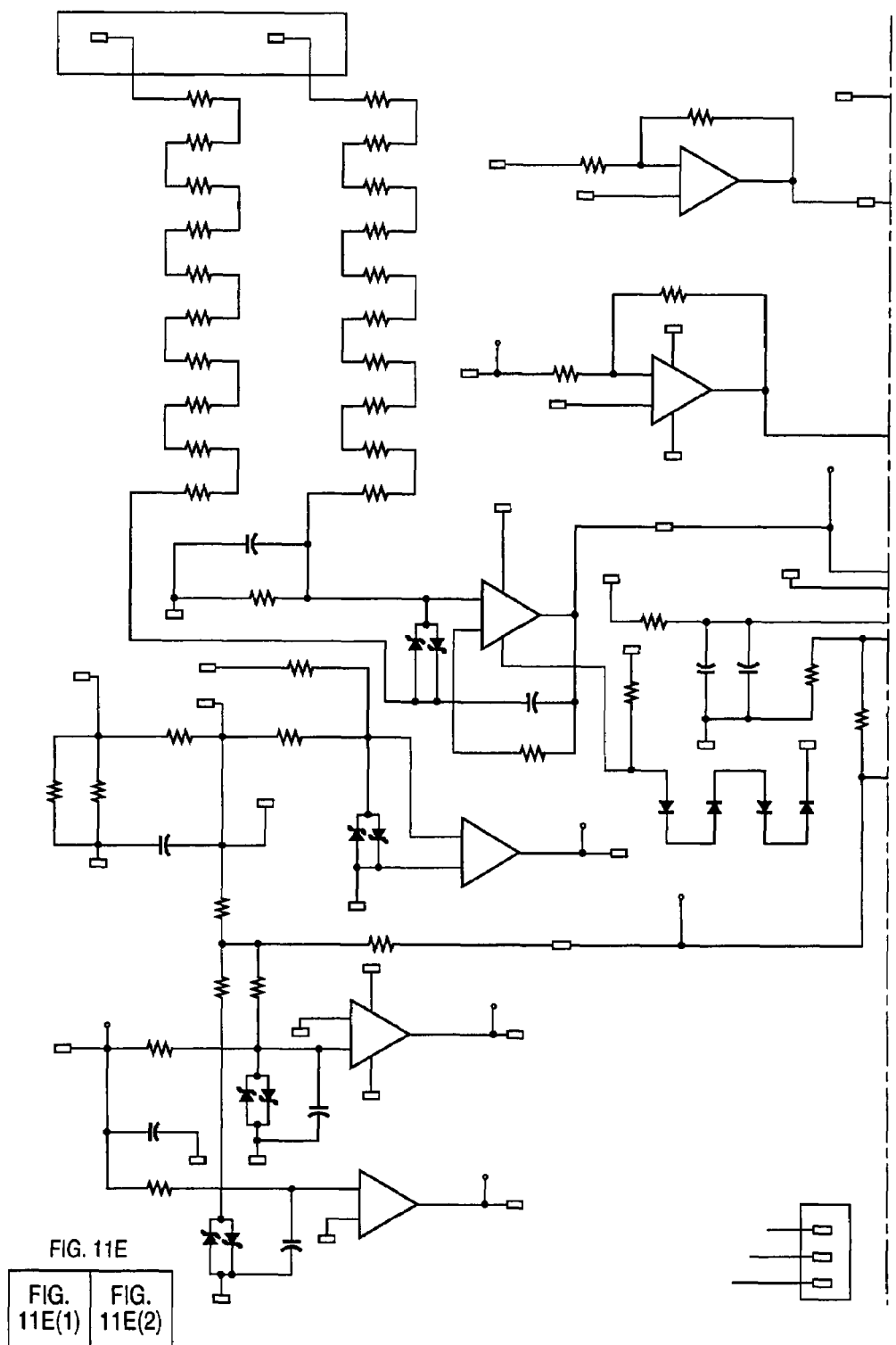
Figure 11F:
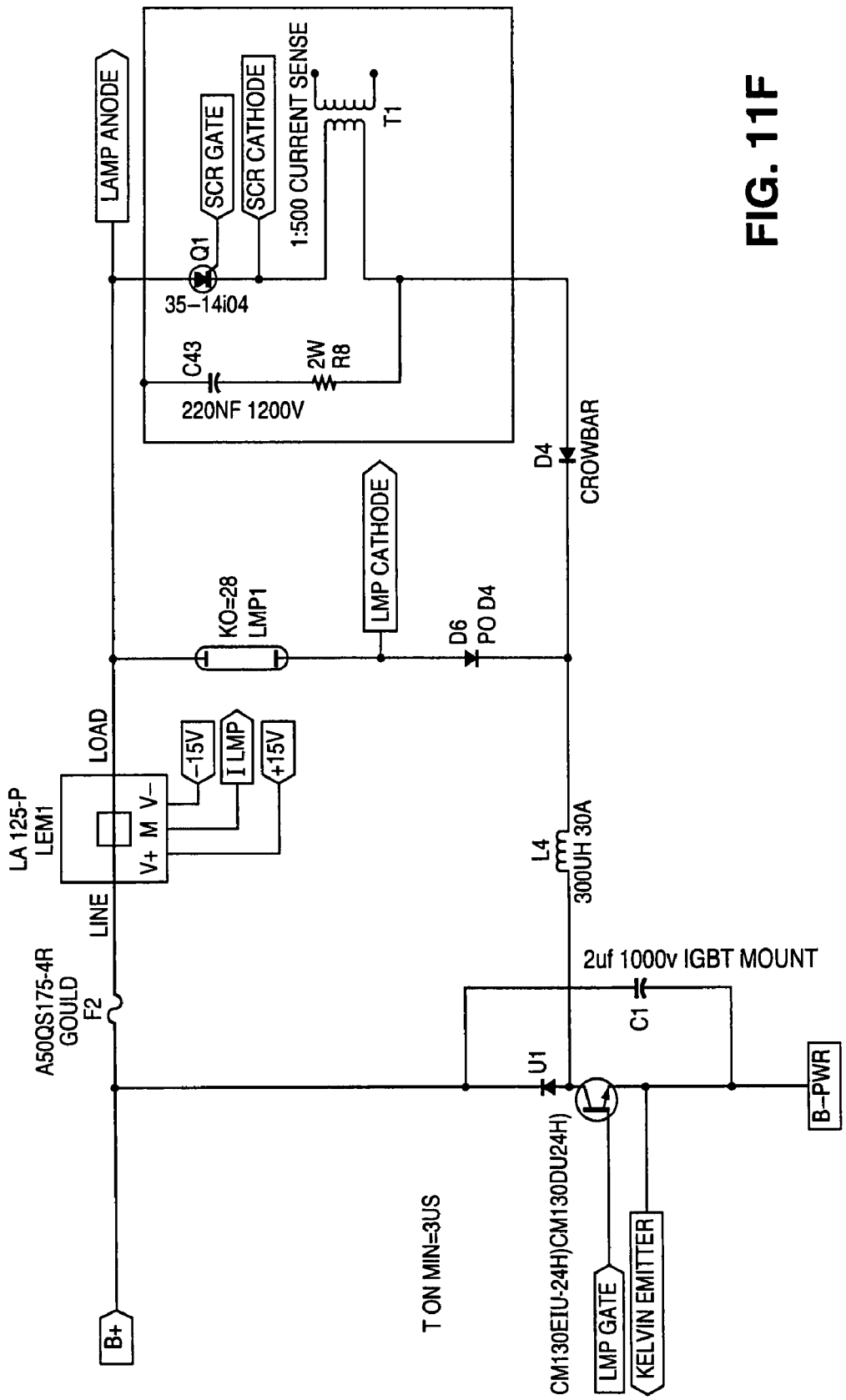
Figure 11G:
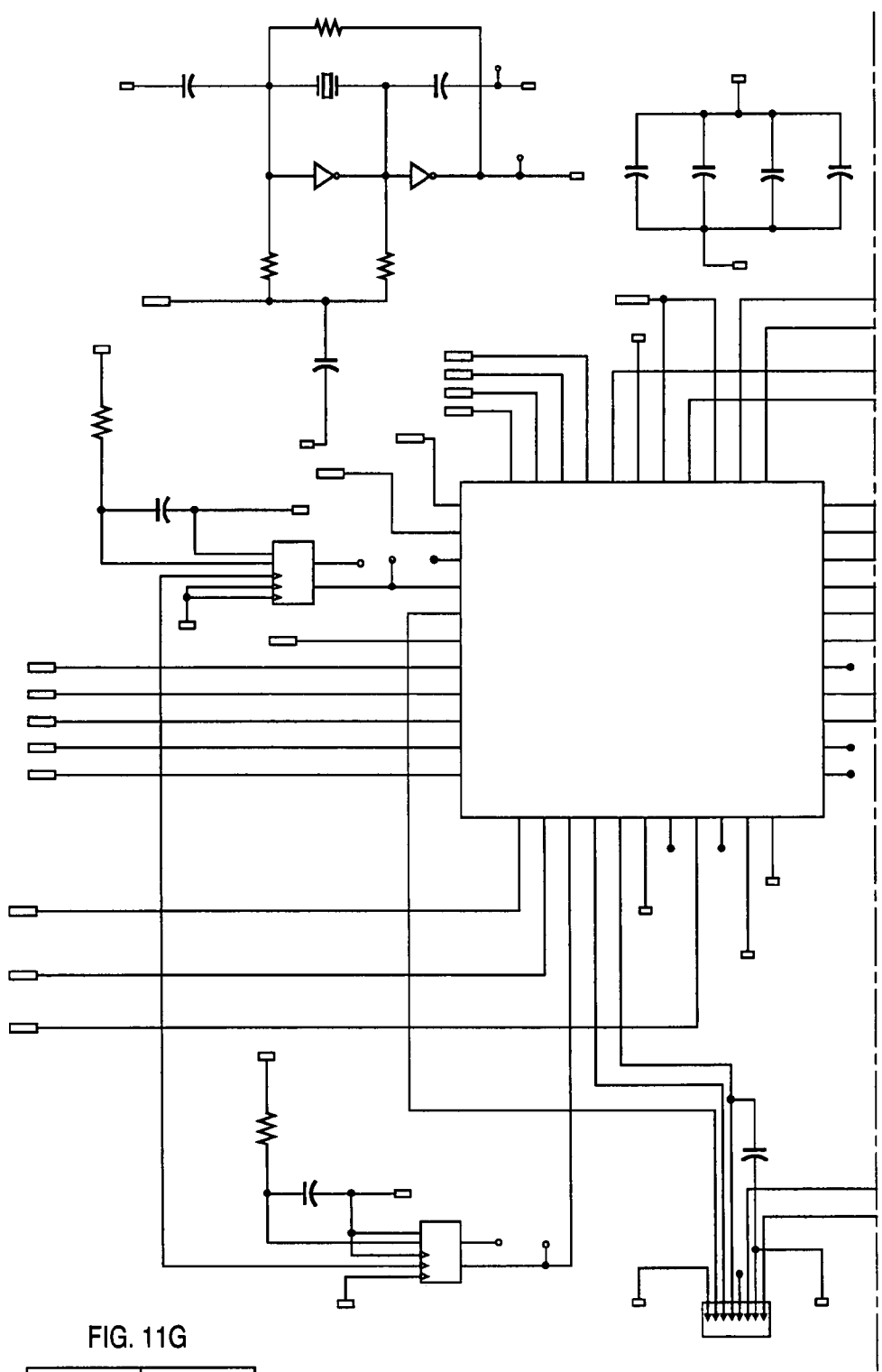
Figure 11H:
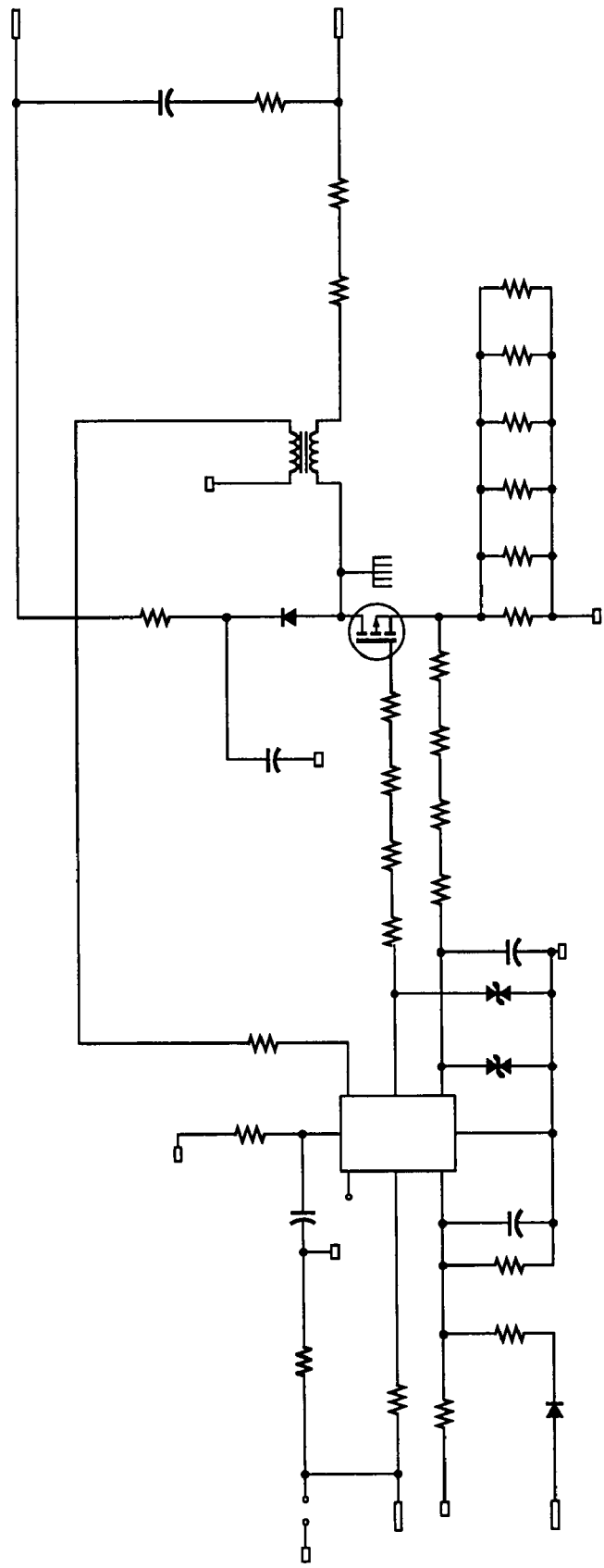
Figure 11I:
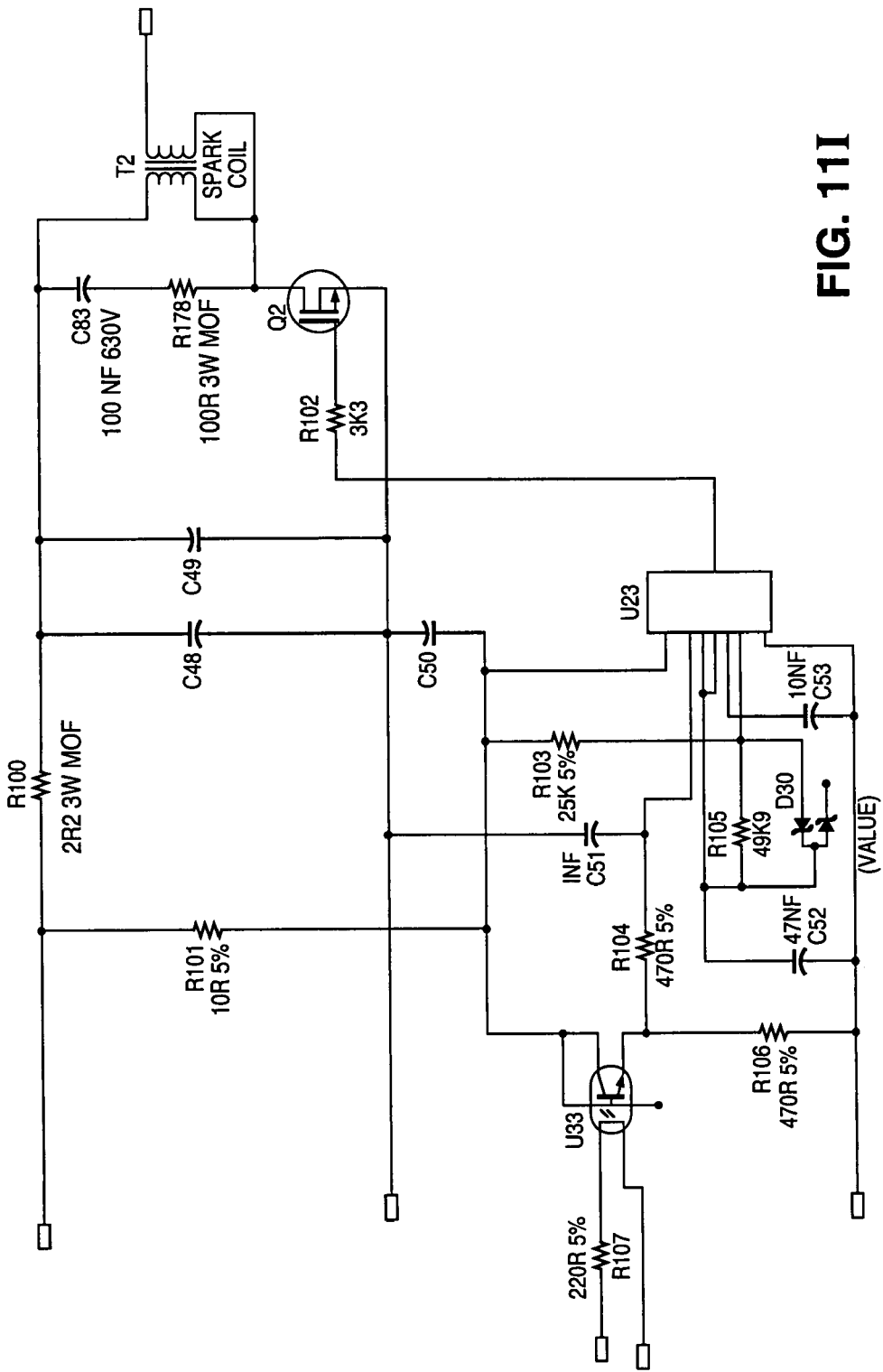
Figure 11J:
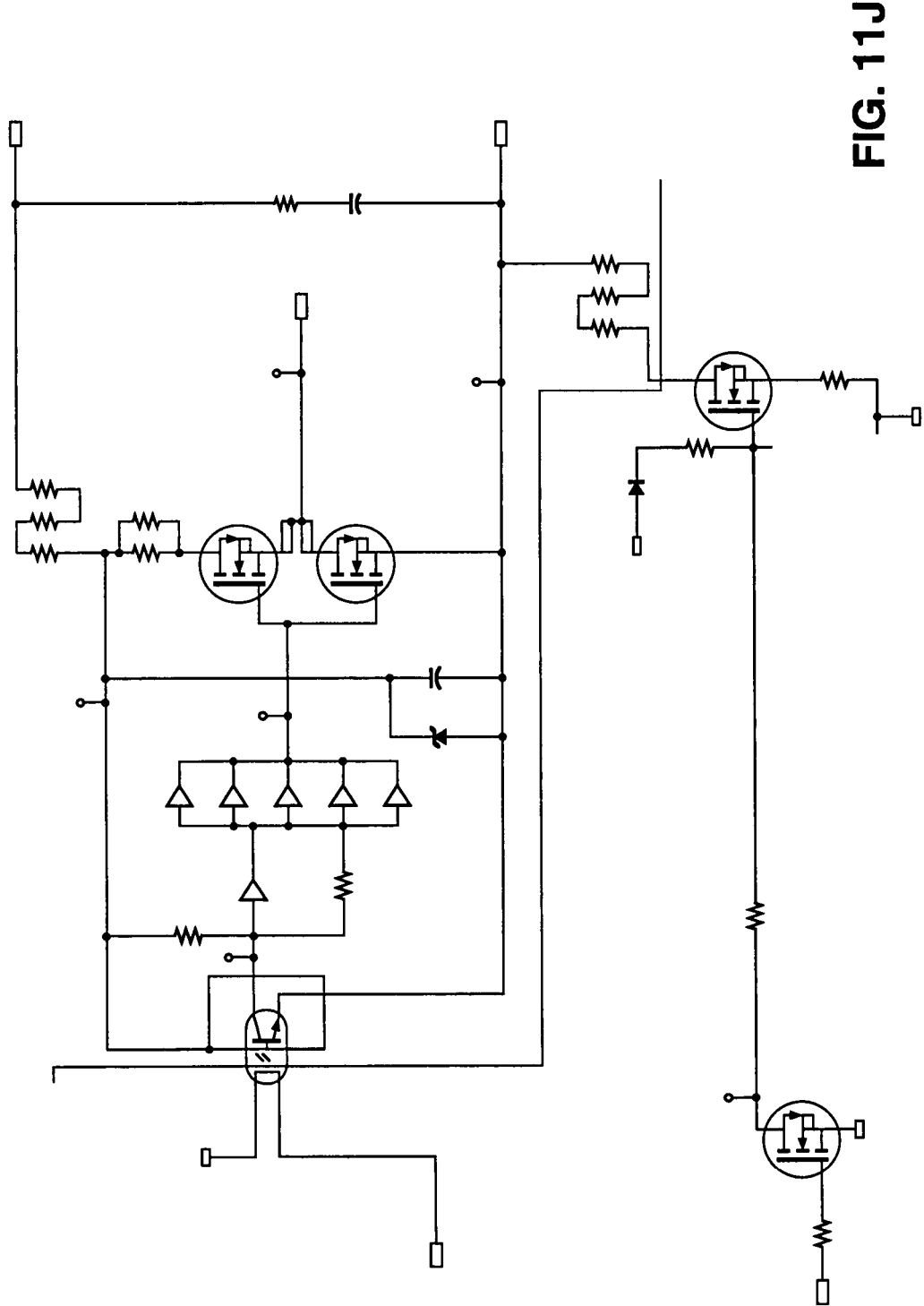
Figure 11K:
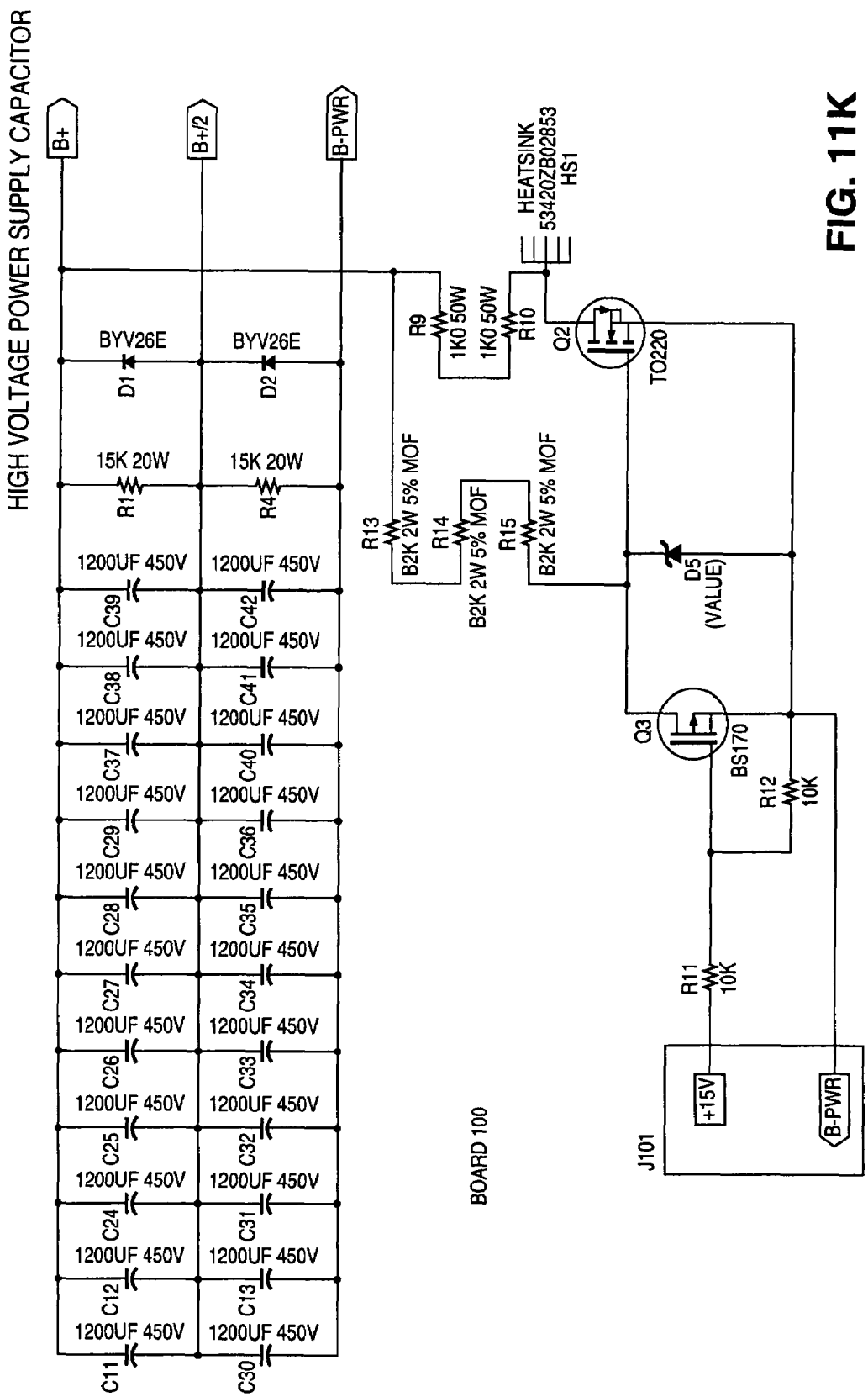

FIG. 10 illustrates another embodiment of the invention in which recessed window 46 is centered between two cooling surfaces 34. This provides two advantages: (1) the practitioner can move device 22 in either direction, back and forth, without having to rotate the handpiece, (2) the trailing cooling surface will reduce both pain and trauma to the skin following the laser exposure. This will be particularly important for the treatment of patients with darker skin types.

Another aspect of the invention relates to the control of the laser-pulse according to the diameter of shaft 4 of hair 2. Part of this selection is based on the belief that laser-pulse duration should be selected to match the thermal relaxation time of the targeted hair. For small diameter hair the pulse should be shorter while for larger diameter hair the pulse should be longer. This belief is used in conjunction with the belief that high peak powers should be avoided. Thus, it is preferred to use longer pulse durations with lower peak powers and to selectively adjust the duration according to the shaft diameter to minimize or eliminate damage to epidermis 10 while not sacrificing heat transfer to hair tissue 20. With this in mind, it is believed that a wavelength in the range of about 800 to 1200 nm would be quite suitable for use with the present invention. For the preferred embodiment a wavelength of 1.06 micron has been chosen. The choice of a 1.06 micron laser is beneficial for many reasons. It permits treating of patient having darker pigmented skin than the shorter wavelength lasers commonly used. The 1.06 micron laser is relatively efficient, requires no special cooling and has the ability to create high pulse energy (such as about 4000 watts in one preferred embodiment) in low duty cycle pulses without large power-consuming support systems. Further the 1.06 micron laser can use flash lamp excitation which can be engineered at a fraction of the cost of high peak power diode lasers.

FIGS. 11A-11K show a power supply coupled with a flash lamp, and the power supply features capacitive reservoir energy storage (FIG. 11K) along with the ability to vary the voltage from the rectified line to an upper limit dictated by the voltage rating of the selected component. For efficiency considerations, the power supply includes power factor correction to minimize losses and high-line current associated with phase differences. The second stage is a boost regulator. The final stage is a buck current regulator (FIG. 11F) which enables pulse amplitude and duration control.

Console 64 is provided with control panel 95 (see FIG. 3) having a number of inputs 96 to provide the desired user control. Inputs 96 include a laser-pulse duration input, which is chosen according to the hair shaft diameter. The laser-pulse duration pulse input could be selected in terms of actual or relative time duration or in terms of actual or relative hair shaft diameter thickness. In addition to the laser pulse duration (hair shaft diameter) input, control panel 96 also includes one or both of a laser-pulse amplitude input or a laser-pulse fluence input. Other inputs to permit other variables to be controlled can also be provided. Console 64 may also include a display 98 to provide the user with information, such as the temperature of cooling surface 34, optimal laser pulse actuation rate, laser-pulse duration selected, etc. In one preferred embodiment control panel 95 includes the following inputs: keyswitch to start the system and turn it off, standby and ready buttons to select the state of operation, controls to select fluence level, pulse width and repetition rate, and emergency-off button; and has the option of displaying the following information: laser and handpiece status (ready/not ready), laser emission indicator, and pulse counter.

In use, the operator first determines the general diameter of the hair to be removed from the patient. Then the laser-pulse duration is selected using the appropriate input 96. In one embodiment, typical hair shaft diameters of about 25 to 150 micrometers will result in laser-pulse durations of about 25 to 150 microseconds. The laser-pulse amplitude or laser-pulse fluence is also selected using an appropriate input 96. After ensuring that the temperature of cooling surface 34 has reached the desired operating temperature, the front end 82 of cooling surface 34 is placed on the initial target area on the patient's skin. To ensure full treatment of the entire area of the skin without missing areas or having excessive overlaps in area, the skin area may be temporarily marked with a set of lines or a grid to help guide device 22. Front end 82 of cooling surface 34 is then placed at a first target area on the patient's skin. Cooling surface 34 typically remains in place from about 0.25 to two seconds. In one preferred embodiment, cooling surface 34 remains in place for one second; after the first second, device 22 is moved in the direction of arrow 80 a distance equal to the length of window 46. After remaining at this position for one second, the user again moves a distance equal to one window length. At this point the first target area has been cooled for the designed two seconds so the target area can be irradiated by pressing fire button 84 during the next one-second interval. Following the firing of a laser and the expiration of the one-second interval, the operator again moves device 22 in the direction arrow 80 one window length and presses fire button 84 to irradiate skin surface 6 thus causing thermal damage to hair tissue 20. The thermal damage is intended to cause most or all of the treated hairs to fall out and preferably not grow back. This procedure continues over the entire treatment area.

Modification and variation can be made to the disclosed embodiments without departing from the subject of the invention as defined in the following claims. While the invention has been described primarily with reference to hair-treatment methods, it may also be useful for other dermatological application.

Any and all patents, patent applications and printed publications referred to above are incorporated by reference.

What is claimed is:

1. A skin treatment system comprising:
a body having a skin-contacting end;
the body having a window through which tissue treating radiation is transmitted to an area of skin being treated;
a radiation source which generates a pulse of tissue treating radiation that is transmitted through the window, and wherein the pulse of tissue treating radiation has a pulse amplitude and a pulse duration; and
a power supply coupled to the radiation source, wherein the power supply includes a buck regulator circuit which controls the pulse amplitude and the pulse duration of the tissue treating radiation;
wherein the radiation source includes a flash lamp;

wherein the power supply includes a capacitor which stores an electrical charge, which is transmitted through the flash lamp and the capacitor is coupled to the flash lamp; and wherein the buck regulator circuit includes a switch which is coupled with the flash lamp, whereby an amount of electrical charge current transmitted through the flash lamp is controlled by an opening and closing of the switch.

2. The system of claim 1, further including a skin-cooling element carried by the body and having a cooling surface at the skin-contacting end.

3. A skin treatment system comprising:
a body having a skin-contacting end;
the body having a window through which tissue treating radiation is transmitted to an area of skin being treated;
a radiation source which generates a pulse of tissue treating radiation that is transmitted through the window, and wherein the pulse of tissue treating radiation has a pulse amplitude and a pulse duration;
a power supply coupled to the radiation source wherein the power supply includes a buck regulator circuit which controls the pulse amplitude and the pulse duration of the tissue treating radiation;
wherein the radiation source includes a flash lamp;
further including a skin-cooling element carried by the body and having a cooling surface at the skin-contacting end;
wherein the power supply includes a capacitor which stores an electrical charge, which is transmitted through the flash lamp and the capacitor is coupled to the flash lamp; and
wherein the buck regulator circuit includes a switch which is coupled with the flash lamp, whereby an amount of electrical charge current transmitted through the flash lamp is controlled by an opening and closing of the switch.

4. The system of claim 3, wherein the buck regulator circuit further includes an inductor coupled between the flashlamp and the switch.

5. The system of claim 4, further including a current sensor coupled between the capacitor and the flash lamp, and control logic which controls opening and closing of the switch based on a signal from the current sensor.

6. The system of claim 5, wherein the switch is an IGBT.

7. A skin treatment system comprising:
a body having a skin-contacting end;
the body having a window through which tissue treating radiation is transmitted to an area of skin being treated;
a radiation source which generates a pulse of tissue treating radiation that is transmitted through the window, and wherein the pulse of tissue treating radiation has a pulse amplitude and a pulse duration;
a power supply coupled to the radiation source, wherein the power supply includes a buck regulator circuit which controls the pulse amplitude and the pulse duration of the tissue treating radiation;
a skin-cooling element carried by the body and having a cooling surface at the skin-contacting end;
wherein the window is laterally offset from the cooling surface, such that the cooling surface is adjacent to the window and aligned with the window along a direction of motion; and
wherein the window is spaced apart from the cooling surface in a direction away from the patient's skin when the cooling surface is contacting the patient's skin so as to create a gap between the window and the patient's skin.

8. A skin treatment system comprising:
a body having a skin-contacting end;
the body having a window through which tissue treating radiation is transmitted to an area of skin being treated;
a radiation source which generates a pulse of tissue treating radiation that is transmitted through the window, and wherein the pulse of tissue treating radiation has a pulse amplitude and a pulse duration;
a power supply coupled to the radiation source wherein the power supply includes a buck regulator circuit which controls the pulse amplitude and the pulse duration of the tissue treating radiation;
a skin-cooling element carried by the body and having a cooling surface at the skin-contacting end;
wherein the radiation source includes a flash lamp;
wherein the power supply includes a capacitor which stores an electrical charge, which is transmitted through the flash lamp and the capacitor is coupled to the flash lamp;
wherein the buck regulator circuit includes a switch and an inductor coupled in series with the flash lamp, whereby an amount of electrical charge current transmitted through the flash lamp is controlled by an opening and closing of the switch;
the power supply further comprising including a current sensor which senses an amount of electrical current which is transmitted through the flashlamp, and the current sensor outputs a signal based on the sensed amount of electrical current; and
wherein the capacitor, the current sensor, the flashlamp, the inductor and switch form an electrical loop and the switch is opened and closed based at least in part on the signal from the current sensor.

9. A skin treatment system comprising:
a body having a skin-contacting end;
the body having a window through which tissue treating radiation is transmitted to an area of skin being treated;
a radiation source which generates a pulse of tissue treating radiation that is transmitted through the window, and wherein the pulse of tissue treating radiation has a pulse amplitude and a pulse duration;
a power supply coupled to the radiation source, wherein the power supply includes a buck regulator circuit which controls the pulse amplitude and the pulse duration of the tissue treating radiation and wherein said radiation source is flashlamp excited laser.

10. The system of claim 9, wherein the radiation source is a neodymium laser.

* * * * *